_(12)_ United States Patent
Guentert et al.

(10) Patent No.: US 11,555,993 B2
(45) Date of Patent: Jan. 17, 2023

(54) CONCEPT FOR A MICROSCOPE SYSTEM WITH AN LED-BASED ILLUMINATION SYSTEM

(71) Applicant: Leica Instruments (Singapore) Pte. Ltd., Singapore (SG)

(72) Inventors: Michael Guentert, Heerbrugg (CH); Ulrich Weiger, Montlingen (CH)

(73) Assignee: Leica Instruments (Singapore) Pte. Ltd., Singapore (SG)

( * ) Notice: Subject to any disclaimer, the term of this patent is extended or adjusted under 35 U.S.C. 154(b) by 0 days.

(21) Appl. No.: 17/191,741

(22) Filed: Mar. 4, 2021

(65) Prior Publication Data

US 2021/0286159 A1 Sep. 16, 2021

(30) Foreign Application Priority Data

Mar. 10, 2020 (DE) .......................... 102020106499.3
Dec. 2, 2020 (EP) ..................................... 20211272

(51) Int. Cl.
*G02B 21/06* (2006.01)
*G02B 21/36* (2006.01)
(Continued)

(52) U.S. Cl.
CPC ............ *G02B 21/06* (2013.01); *A61B 5/0071* (2013.01); *A61B 5/0077* (2013.01); *G02B 21/08* (2013.01);
(Continued)

(58) Field of Classification Search
CPC .... A61B 2017/00203; A61B 2090/309; A61B 2505/05; A61B 5/0035; A61B 5/0071;
(Continued)

(56) References Cited

U.S. PATENT DOCUMENTS

2009/0002813 A1   1/2009  Soon
2009/0153797 A1*  6/2009  Allon .................... A61B 3/12
                                                                 362/11
(Continued)

FOREIGN PATENT DOCUMENTS

DE   102009025127 A1   12/2010
DE   102014112285 A1   3/2016
(Continued)

OTHER PUBLICATIONS

Wegerhoff Rainer et al: "Basics of Light Microscopy Imaging & Imaging Microscopy" (Jan. 20, 2011), XP055825048, Retrieved from the Internet: URL:https://www.embl.de/services/core_facilities/almf/events_ext/Basics_of_Light_microscopy_GIT.pdf [retrieved on Jul. 16, 2021], * sections "Colour temperature and white balance" and "Automated white balance adjustments"*.

*Primary Examiner* — Behrooz M Senfi
*Assistant Examiner* — Kathleen M Walsh
(74) *Attorney, Agent, or Firm* — 2SPL Patent Attorneys PartG mbB; Kieran O'Leary

(57) ABSTRACT

Examples relate to a microscope system comprising a Light-Emitting Diode (LED)-based illumination system and at least one image sensor assembly, and to a corresponding system, method and computer program. The LED-based illumination system is configured to emit radiation power having at least one peak at a wavelength that is tuned to an excitation wavelength of at least one fluorescent material and/or to emit radiation power across a white light spectrum, with the light emitted across the white light spectrum being filtered such that light having a wavelength spectrum that coincides with at least one fluorescence emission wavelength spectrum of the at least one fluorescent material is attenuated or blocked. The at least one image sensor assembly is configured to generate image data, with the image data (at least) representing light reflected by a sample that is (Continued)

illuminated by the LED-based illumination system. The microscope system comprises one or more processors, configured to process the image data to generate processed image data.

18 Claims, 24 Drawing Sheets

(51) Int. Cl.
*H04N 5/235* (2006.01)
*G02B 21/08* (2006.01)
*G02B 21/16* (2006.01)
*A61B 5/00* (2006.01)

(52) U.S. Cl.
CPC .......... *G02B 21/16* (2013.01); *G02B 21/361* (2013.01); *G02B 21/365* (2013.01); *H04N 5/2354* (2013.01)

(58) Field of Classification Search
CPC ....... A61B 5/0077; A61B 90/20; A61B 90/30; G02B 21/0012; G02B 21/06; G02B 21/08; G02B 21/082; G02B 21/16; G02B 21/361; G02B 21/365; H04N 5/2354
USPC .......................................................... 349/79
See application file for complete search history.

(56) References Cited

U.S. PATENT DOCUMENTS

| | | | | |
|---|---|---|---|---|
| 2009/0201577 | A1* | 8/2009 | LaPlante | G01N 21/6458 313/501 |
| 2009/0236541 | A1* | 9/2009 | Lomnes | A61B 1/0646 250/362 |
| 2012/0085932 | A1* | 4/2012 | Themelis | G01J 3/513 356/407 |
| 2012/0326055 | A1* | 12/2012 | Wilson | A61B 5/0059 250/459.1 |
| 2017/0167980 | A1* | 6/2017 | Dimitriadis | A61B 3/14 |
| 2017/0202633 | A1* | 7/2017 | Liu | G16H 40/63 |
| 2017/0209050 | A1* | 7/2017 | Fengler | H04N 5/238 |
| 2018/0177399 | A1* | 6/2018 | Ntziachristos | A61B 5/0068 |
| 2019/0170647 | A1* | 6/2019 | Ikenaga | G01N 21/6458 |
| 2021/0286160 | A1* | 9/2021 | Guentert | A61B 90/30 |

FOREIGN PATENT DOCUMENTS

| | | | |
|---|---|---|---|
| EP | 2359745 A1 * | 8/2011 | ......... A61B 1/00009 |
| EP | 2359745 A1 | 8/2011 | |
| JP | H10201707 A | 8/1998 | |
| JP | 2007090044 A | 4/2007 | |
| JP | 2008-209726 A | 9/2008 | |
| JP | 2013-057750 A | 3/2013 | |
| JP | 2013519867 A | 5/2013 | |
| JP | 2017526899 A | 9/2017 | |
| JP | 2018027272 A | 2/2018 | |
| WO | 2019158168 A1 | 8/2019 | |

* cited by examiner

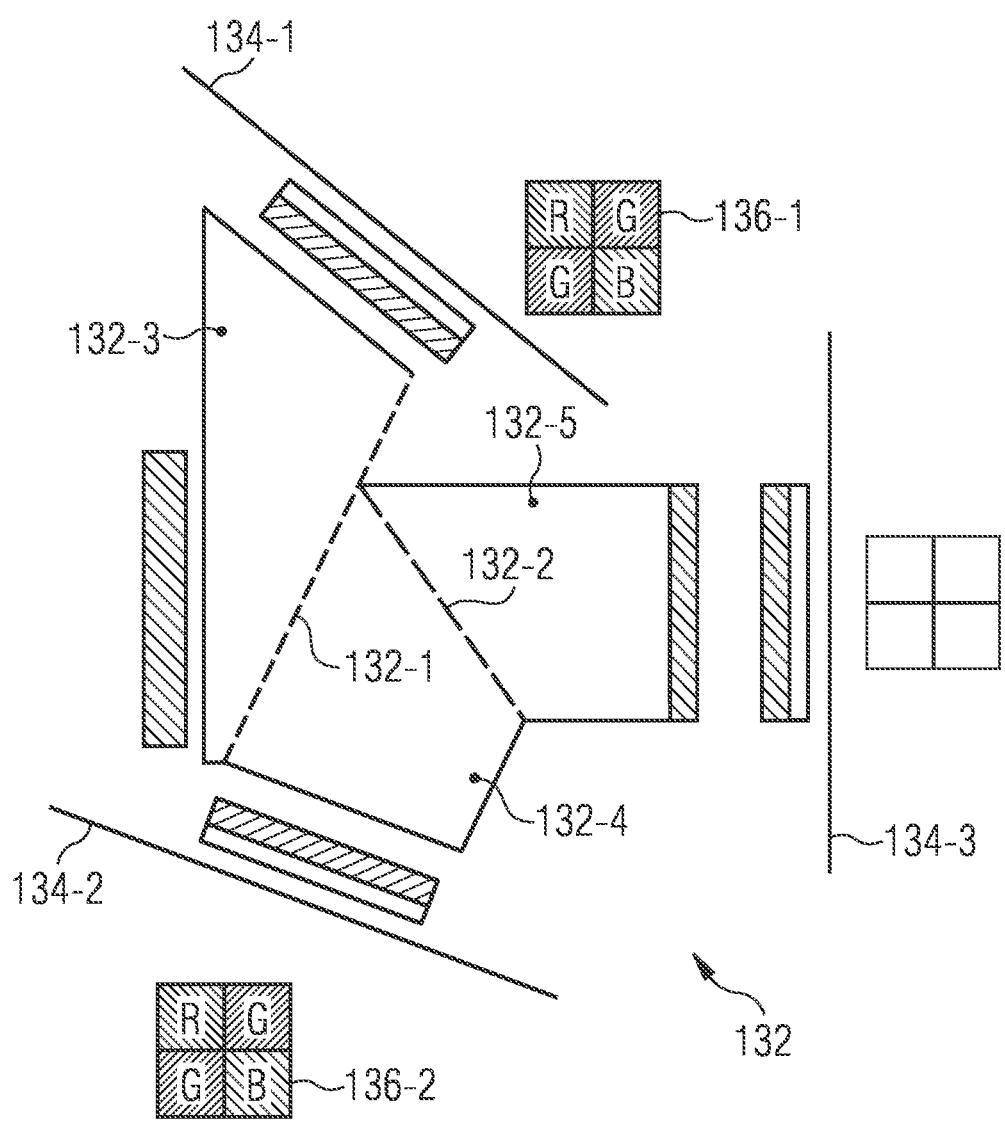

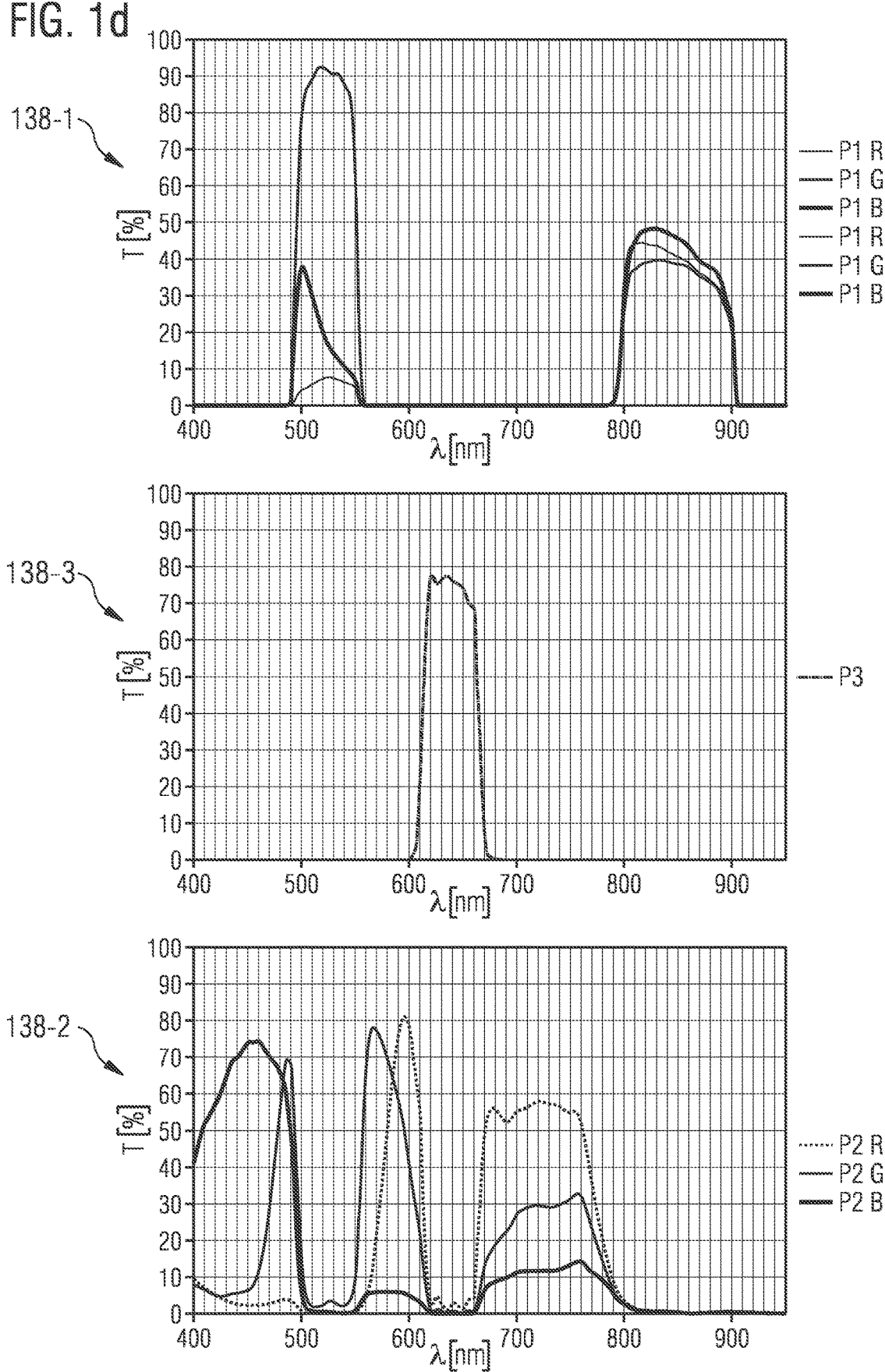

| FIG. 6a | | |
|---|---|---|
| FIG. 6a-1 | FIG. 6a-2 | FIG. 6a-3 |

| FIG. 6b-1 | FIG. 6b-2 | FIG. 6b-3 |

| FIG. 6c | | |
|---|---|---|
| FIG. 6c-1 | FIG. 6c-2 | FIG. 6c-3 |

| FIG. 6d | | |
|---|---|---|
| FIG. 6d-1 | FIG. 6d-2 | FIG. 6d-3 |

CONCEPT FOR A MICROSCOPE SYSTEM WITH AN LED-BASED ILLUMINATION SYSTEM

TECHNICAL FIELD

Examples relate to a microscope system comprising a Light-Emitting Diode (LED)-based illumination system and at least one image sensor assembly, and to a corresponding system, method and computer program.

BACKGROUND

In many microscope systems, Xenon-based illumination is used. To obtain light in different wavelength bands, the light of a Xenon-based light source is passed through a filter, e.g. through a filter wheel. This may lead to bulky, inefficient systems with high heat dissipation, which often rely on a fiber bundle from the stand to the carrier to provide the illumination at the carrier. Also, such a setup is inflexible, as the Xenon light source is used for both white light reflectance illumination and for fluorescence excitation, albeit using different filter wheels.

Furthermore, depending on the illumination provided by the illumination system of the microscope, different types of imaging may be performed, such as reflectance imaging and fluorescence imaging. However, due to the illumination provided through the different filter wheels, the illumination being used for reflectance imaging may contain gaps, which may manifest within the "white light" reflectance images.

SUMMARY

There may be a desire for an improved concept for a microscope system comprising an illumination system and an imaging sensor.

This desire is addressed by the subject-matter of the independent claims.

Various embodiments of the present disclosure are based on the finding that it may be desirable to design the illumination system, the imaging sensor(s) and the image processing of a microscope system as an interdependent system. For example, the imaging sensor or sensors may be tuned (e.g. using bandpass filters) to the wavelength bands provided by the illumination system. The radiation power may be provided by the illumination system using Light-Emitting Diodes (LED), with illumination spectra that are tailored to the specific needs of white light and fluorescence imaging, and with light sources that permit an independent activation of different illumination spectra. Furthermore, image processing may be performed that compensates, in white light imaging, for portions of the spectrum that are being used for fluorescence imaging, and that performs fluorescence imaging using the portions of the spectrum not presently used for white light imaging.

Various embodiments of the present disclosure relate to a microscope system comprising an LED-based illumination system, configured to emit radiation power (i.e. light) having at least one peak at a wavelength that is tuned to an excitation wavelength of at least one fluorescent material and/or to emit radiation power (i.e. light) across a white light spectrum, with the radiation power emitted across the white light spectrum being filtered such that light having a wavelength (spectrum) that coincides with at least one fluorescence emission wavelength (spectrum) of the at least one fluorescent material is attenuated or blocked. The microscope system comprises at least one image sensor assembly configured to generate image data. The image data (at least) represents light reflected by a sample that is illuminated by the LED-based illumination system. The microscope system comprises one or more processors configured to process the image data to generate processed image data. Using the system, processed image data may be output that shows a reflectance image across the white light spectrum, based on an illumination that excludes some parts of the spectrum to account for fluorescence imaging. Additionally, a fluorescence image overlay may be generated. By using LED-based light sources, the energy consumption, and thus the heat dissipation may be reduced. Furthermore, as LED-based light sources are compact, they can be included near the objective of the microscope, instead of using fiber channels to transport the light to the carrier.

In various examples, the one or more processors are configured to reconstruct a portion of the processed image data representing light having a wavelength that coincides with the at least one fluorescence emission wavelength of the at least one fluorescent material. In other words, image processing may be used to compensate for the "missing" portion of the spectrum.

In various examples, the microscope system is used for both reflectance imaging and fluorescence imaging. Accordingly, the image data may represent the light reflected by the sample that is illuminated by the LED-based illumination system and light emitted by the at least one fluorescent material. Thus, the one or more processors may be configured to perform image processing on the light reflected by the sample that is illuminated by the LED-based illumination system, and separately on the light emitted by the at least one fluorescent material For example, the one or more processors may be configured to generate a first image representing visible light and a second image representing fluorescence emissions of the at least one fluorescent material based on the image data. In other words, the one or more processors may be configured to perform, using the image data provided by the at least one image sensor assembly, reflectance imaging and fluorescence imaging.

However, the microscope system might, in some cases, only provide one of the images. For example, the LED-based illumination system may have two or more modes of operation. The first mode of operation may be suitable for reflectance imaging and fluorescence imaging. The second mode of generation may be suitable for reflectance imaging (only, without fluorescence imaging). The one or more processors may be configured to generate the first image and the second image if the LED-based illumination system operates in the first mode of operation, and to generate the first image without generating the second image if the LED-based illumination system operates in the second mode of operation. In some examples, the LED-based illumination system may also have a third mode of operation being suitable for fluorescence imaging only. In this case, the one or more processors might only provide the second image.

In various examples, the microscope system comprises two image sensor assemblies, e.g. to provide stereoscopic imaging.

In some examples, image sensor assemblies may be used that comprise multiple sensors, e.g. to capture different portions of the spectrum. In various examples, these sensors may be coupled with a beam-splitter assembly that is used to guide the relevant portions of the spectrum to the respective image sensors. In other words, the at least one image sensor assembly, or each image sensor assembly, may comprise a beam-splitter assembly and three image sensors.

The beam-splitter assembly may be configured to guide light of a first spectral portion to the first image sensor, light of a second spectral portion to the second image sensor and light of a third spectral portion to the third image sensor. The three image sensors may be configured to generate image data based on the spectral portions that are incident to the respective image sensors. With a three-sensor setup, and a separation of the light into the three spectral portions that is tuned to various emission wavelength bands of fluorophores, reflectance imaging of light in the visible light wavelength band and fluorescence imaging (with multiple fluorophores) can be performed at the same time, while retaining good image quality on the white light image.

For example, a first and a second of the three image sensors may be operated with Bayer filters, and a third of the three image sensors may be operated without a Bayer filter. For example, the image sensors that are equipped with Bayer filters may be used to image portions of the spectrum that cover a wider range of the spectrum, e.g. different colors, while the sensor that is operated without the Bayer filter may be used to image a single portion of a spectrum.

In various examples, the image data comprises a first portion originating from the first image sensor, a second portion originating from the second image sensor, and a third portion originating from the third image sensor. The one or more processors may be configured to generate a first image representing visible light based on a first combination of the three portions of the image data, and to generate a second image representing fluorescence emissions of the at least one fluorescent material based on a second combination of the three portions of the image data. In other words, the image data provided by the respective sensors may be combined differently, depending on the type of image being generated.

For example, the one or more processors may be configured to combine the three portions of the image data such that, if light is emitted having one peak at a wavelength that is tuned to an excitation wavelength of one fluorescent material, the first image is generated based on two portions of the image data and the second image is generated based on one portion of the image data. The one or more processors may be configured to combine the three portions of the image data such that, if light is emitted having three peaks at three wavelengths that are tuned to excitation wavelengths of three fluorescent materials, the first image is generated based on one portion of the image data and the second image is generated based on two portions of the image data.

If light is emitted having two peaks at wavelengths that are tuned to two excitation wavelengths of two fluorescent materials, it depends on which fluorophores are being used—in some cases, the first image is generated based on two portions of the image data and the second image is generated based on one portion of the image data (e.g. if both excitation wavelengths are covered by one of the image sensors), and in some cases, the first image is generated based on one portion of the image data and the second image is generated based on two portions of the image data (e.g. if the two excitation wavelengths are covered by different image sensors).

In various examples, different image sensors may be used to perform fluorescence imaging of different fluorophores. For example, the one or more processors may be configured to combine the three portions of the image data such, that, if light is emitted having a peak at a first wavelength that is tuned to an excitation wavelength of a first fluorescent material, the second image is generated based on the first portion of the image data. he one or more processors may be configured to combine the three portions of the image data such, that, if light is emitted having a peak at a second wavelength that is tuned to an excitation wavelength of a second fluorescent material, the second image is generated based on the third portion of the image data.

However, one of the portions of the image data may be used to perform fluorescence imaging of two fluorophores. For example, the one or more processors may be configured to combine the three portions of the image data such, that, if light is emitted having a peak at a third wavelength that is tuned to an excitation wavelength of a third fluorescent material, the second image is generated based on the first portion of the image data.

In various examples, the one or more processors are configured to generate the first image at least based on the second portion of the image data. In other words, the second portion of the image data might always be used to generate the "white light" reflectance image, and might not be used to generate the fluorescence image.

In various examples, at least one of the first and the second spectral portion comprises two spectral subportions spaced apart from each other. For example, these two spectral subportions may be used to perform fluorescence imaging of two different fluorophores using the same image sensors. For example, the first spectral portion may comprise two continuous sub-portions located between 450 nm and 550 nm and between 750 nm and 1000 nm. The third spectral portion may be a continuous portion that is located between 550 nm and 700 nm. For example, the first spectral portion may be used to perform fluorescence imaging of Fluorescein (in the range between 450 nm and 550 nm) and of Indo-Cyanine Green (ICG, in the range between 750 nm and 1000 nm). The third spectral portion may be used to perform fluorescence imaging of 5-ALA.

As is evident from the name, the LED-based illumination system comprises LED-based light sources. In particular, the LED-based illumination system may comprise one or more first LED-based light sources configured to emit radiation power (i.e. light) across the white light color spectrum. The LED-based illumination system may comprise at least one optical filter that is arranged to filter the light emitted by the one or more first LED-based light sources and configured to attenuate or block light having a wavelength that coincides with the at least one fluorescence emission wavelength of the at least one fluorescent material. The LED-based illumination system may comprise one or more second LED-based light sources configured to emit the light having at least one peak at a wavelength that is tuned to an excitation wavelength of at least one fluorescent material. The two groups of light sources can be used to independently control the illumination for white light and fluorescence excitation. The filter may be used to block or attenuate light at wavelengths that coincide with an emission spectrum of the fluorescent material, so the emissions of the fluorescent material can be distinguished within image data while the white light LED sources are active.

In various examples, the one or more second LED-based light sources are configured to emit radiation power (i.e. light) having a peak at one or more of between 390 nm and 420 nm, between 460 nm and 500 nm, and between 780 nm and 810 nm. These wavelengths are excitation wavelengths of common fluorophores.

In some examples, the LED-based illumination system further comprises one or more third LED-based light sources configured to emit radiation power (i.e. light) across the white light color spectrum. These additional light sources may be used to provide white light that is not filtered by the at least one optical filter, e.g. if only reflectance imaging is being performed.

In various examples, the LED-based illumination system has two or more modes of operation. The LED-based illumination system may be configured to, in a first mode of operation, emit the radiation power (i.e. light) having at least one peak at a wavelength that is tuned to the excitation wavelength of at least one fluorescent material and the radiation power across the white light spectrum, with the light emitted across the white light spectrum being filtered such that light having a wavelength that coincides with the at least one fluorescence emission wavelength of the at least one fluorescent material is attenuated or blocked, and, in a second mode of operation, to emit radiation power (i.e. light) across the white light spectrum without light having a wavelength that coincides with the at least one fluorescence emission wavelength of the at least one fluorescent material being attenuated or blocked. In other words, in the second mode of operation, the entire visible light spectrum may be illuminated.

Various embodiments of the present disclosure further provide a method for imaging an object using a microscope. The method comprises emitting, using an LED-based illumination system, radiation power (i.e. light) having at least one peak at a wavelength that is tuned to an excitation wavelength of at least one fluorescent material. The method comprises emitting, using the LED-based illumination system, radiation power (i.e. light) across a white light spectrum. The light emitted across the white light spectrum being filtered such that light having a wavelength (spectrum) that coincides with at least one fluorescence emission wavelength (spectrum) of the at least one fluorescent material is attenuated or blocked. The method comprises generating image data, the image data representing light reflected by a sample that is illuminated by the LED-based illumination system. The method comprises processing the image data to generate processed image data.

Various embodiments of the present disclosure relate to a computer program with a program code for performing the method when the computer program is executed on a processor.

SHORT DESCRIPTION OF THE FIGURES

Some examples of apparatuses and/or methods will be described in the following by way of example only, and with reference to the accompanying figures, in which FIG. 1a shows a schematic diagram of an example of a microscope system;

DETAILED DESCRIPTION

Various examples will now be described more fully with reference to the accompanying drawings in which some examples are illustrated. In the figures, the thicknesses of lines, layers and/or regions may be exaggerated for clarity.

Figure 1A:
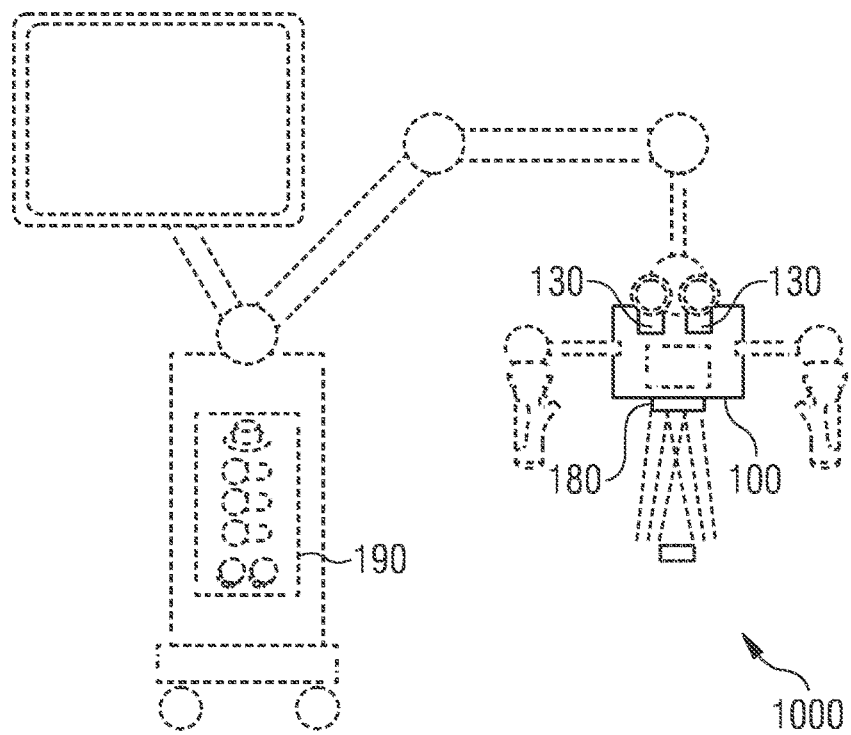
FIG. 1b shows a schematic diagram of an example of an illumination system for a microscope.
FIG. 1c shows a schematic diagram of an example of an image sensor assembly for a microscope.
FIG. 1d shows a schematic diagram of an example of three spectral portions.

FIG. 1a shows a schematic diagram of an example of a microscope system 1000. The microscope system comprises an LED-based illumination system 180, configured to emit radiation power having at least one peak at a wavelength that is tuned to an excitation wavelength of at least one fluorescent material and/or to emit radiation power across a white light spectrum. The light emitted across the white light spectrum is filtered such that light having a wavelength spectrum that coincides with at least one fluorescence emission wavelength spectrum of the at least one fluorescent material is attenuated or blocked. The microscope system comprises at least one image sensor assembly 130 configured to generate image data, the image data representing light reflected by a sample that is illuminated by the LED-based illumination system. The microscope system comprises one or more processors 194, configured to process the image data to generate processed image data.

The microscope system 1000 of FIG. 1a is a surgical microscope system, i.e. a microscope system for use during surgery of a patient. Such a microscope system further comprises a microscope 100, which is also denoted "optics carrier" 100, as it comprises the optical components of the microscope system. In general, a distinction is made between the actual microscope, and the microscope system comprising the microscope, with the microscope system comprising the microscope and various components that are used in conjunction with the microscope, e.g. the illumination system, an auxiliary display, an arm etc. In a microscope system, the actual microscope is often also referred to as the "optics carrier", as it comprises the optical components of the microscope system. In general, a microscope is an optical instrument that is suitable for examining objects that are too small to be examined by the human eye (alone). For example, a microscope may provide an optical magnification of an object. In modern microscopes, the optical magnification is often provided for a camera or an imaging sensor, such as the at least one image sensor assembly 130. The microscope may further comprise one or more optical magnification components that are used to magnify a view on the sample.

Figure 1B:
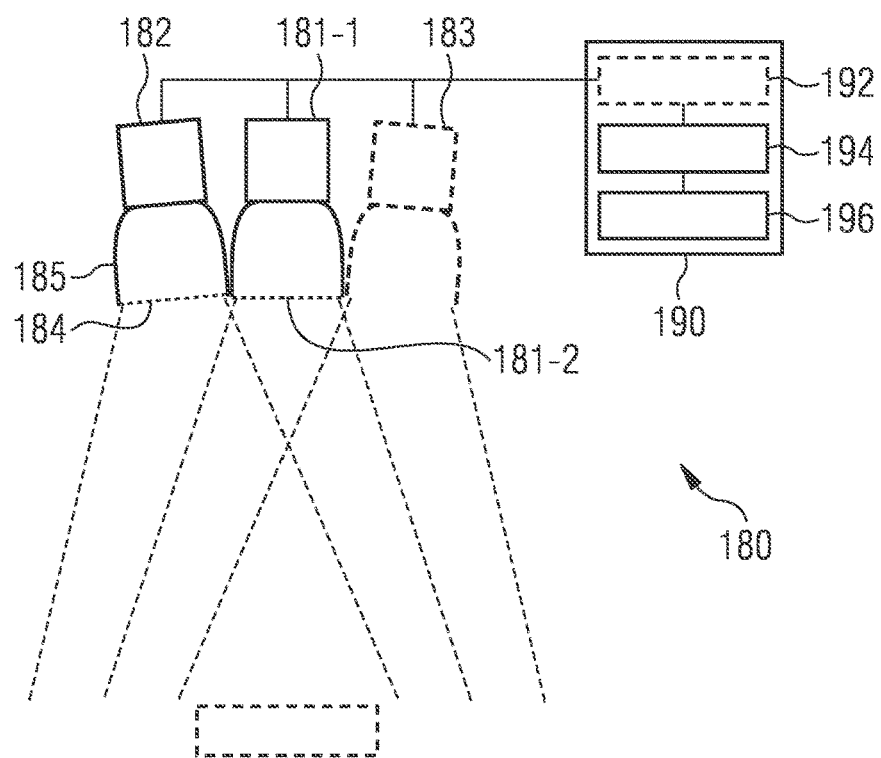

Various examples of the microscope system may further comprise, as shown in FIG. 1a and 1b, a system 190 for the microscope, i.e. a computer system for the microscope. The system 190 may for example comprise the one or more processors 194 of the microscope system. In general, the system for the microscope may be coupled with various components of the microscope system and/or of the microscope system, and may be configured to perform data and signal processing for the microscope or microscope system. For example, as shown in FIG. 1b, the system 190 may comprise the one or more processors 194 and one or more storage devices 196. Optionally, the system 190 may further comprise an interface 192 for communicating with the other components of the microscope or microscope system. For example, as shown in FIG. 1b, the interface may be configured to communicate with the illumination system 180 and/or with the two or more image sensor assemblies 130. Optionally, the interface may also be used to communicate with other components of the microscope system or microscope, such as the arm, an auxiliary display, a touch-screen control display, handles, a foot pedal etc. In general, the functionality of the system 190 may be provided by the one or more processors, e.g. in conjunction with the interface 192 (for exchanging information or signals) and/or with the one or more storage devices (for storing information).

The microscope system comprises the Light Emitting Diode, LED,-based illumination system 180, configured to emit radiation power having at least one peak at a wavelength that is tuned to an excitation wavelength of at least one fluorescent material and/or to emit radiation power across a white light spectrum. In various examples, the term "emit radiation power is used for the actual light sources, as the light sources are configured to emit (electromagnetic) radiation within the spectrum that is defined as "light". In other words, the respective light sources may emit radiation power that manifests itself as light. Consequently, the light sources, and thus the LED-based illumination system, may be deemed to emit light in the various bands specified above and/or below.

Figure 2A:
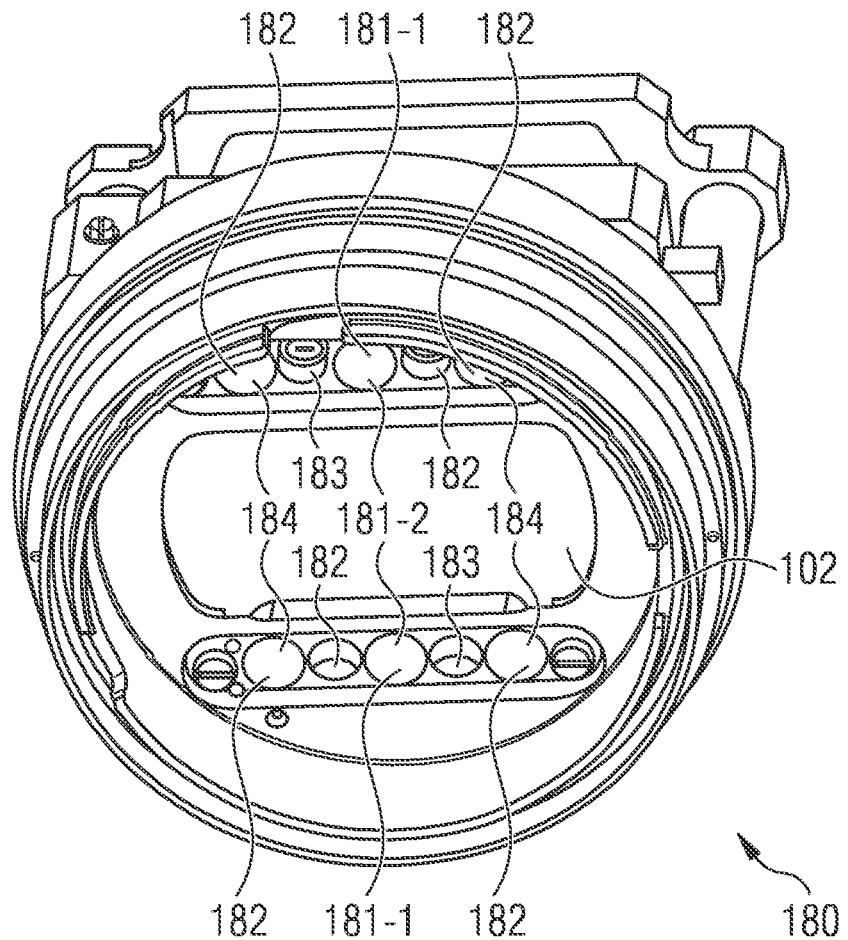
FIGS. 2a and 2b show schematic diagrams of examples of a microscope system.
Figure 2B:
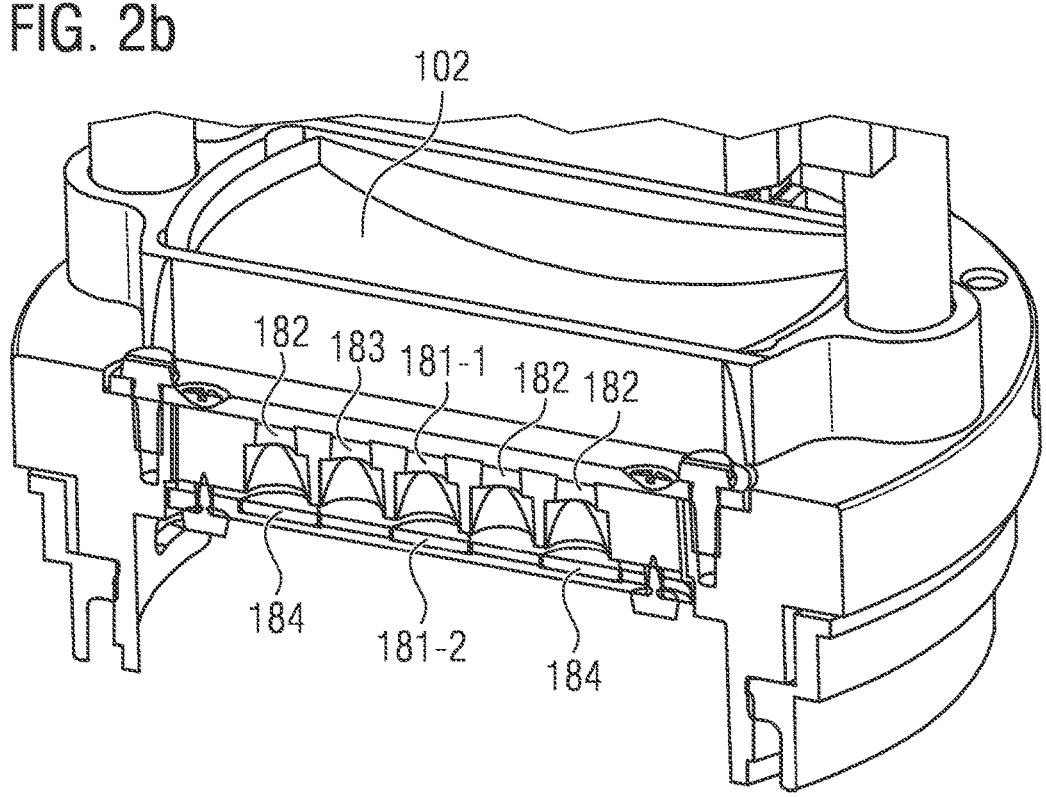

FIG. 1b shows a schematic diagram of an example of an illumination system 180 for a microscope. The illumination system 180 is an LED-based illumination system 180 that is suitable for microscope. For example, the illumination system 180 shown in FIG. 1b may be integrated within the microscopes and/or microscope systems shown in connection with FIGS. 1a, 2a, 2b and 4 to 7. Particularly, the illumination system 180 shown in FIG. 1b may be located at an objective 102, as shown in FIGS. 2a and 2b, of the microscope.

The illumination system 180 of FIG. 1b is an LED-based illumination system being configured to emit radiation power having at least one peak at a wavelength that is tuned to an excitation wavelength of at least one fluorescent material and/or to emit radiation power across a white light spectrum.

For example, the illumination system shown in FIG. 1b comprises one or more first LED-based light sources 181-1. The one or more first LED-based light sources are configured to emit radiation power across a white light color spectrum. The illumination system comprises at least one optical filter 181-2. The at least one optical filter is arranged to filter the light emitted by the one or more first LED-based light sources. For example, the light emitted across the white light spectrum may be filtered such that light having a wavelength spectrum that coincides with at least one fluorescence emission wavelength spectrum of the at least one fluorescent material is attenuated or blocked. Consequently, the light emitted across the white light spectrum is filtered such that light having a wavelength spectrum that coincides with at least one fluorescence emission wavelength spectrum of the at least one fluorescent material is attenuated or blocked. The illumination system of FIG. 1b comprises one or more second LED-based light sources 182. The one or more second LED-based light sources are configured to provide light having at least one peak at a wavelength that is tuned to an excitation wavelength of at least one fluorescent material. Each LED-based light source 181-1; 182 (and optionally 183) may be configured to emit radiation power towards a sample to be observed via the microscope.

In microscope systems, illumination systems are generally used to illuminate the sample, e.g. a sample on a sample stage (in case of a laboratory microscope), or a patient on an operating table. Consequently, the light sources 181-1 and 182 (and, as introduced below, 183) may be configured to emit radiation power towards the sample to be observed via the microscope. In other words, the light emitted by the light sources may be directed at the sample, e.g. at the sample stage, or towards the patient. To avoid an overly wide beam angle of the light source, optical concentration elements 185 may be used to direct the light towards the sample. In other words, each LED-based light source may be configured to emit the light towards the sample through an optical concentration element. In general, different kinds of optical concentration elements may be used, such as lenses, light guides, or parabolic concentrators. For example, compound parabolic concentrators may be used. In other words, the optical concentration element may be a compound parabolic concentrator (CPC), e.g. Total Internal Reflection (TIR)-based CPC. Compound parabolic concentrators are optical elements, having a hollow and parabolic shape, that are suitable for collecting and concentrating light from light sources, and that yield a pre-defined maximal angle at which the light is emitted from the compound parabolic concentrator. For example, each light source may be coupled with a compound parabolic concentrator, and the light of the light sources may be concentrated by the compound parabolic concentrator coupled with the light sources.

In general, the light sources being used in embodiments of the present disclosure are LED-based light sources. In general, an LED-based light source may comprise an LED, e.g. a surface mounted LED (i.e. a SMD LED), and a connection structure for electrically connecting the LED to an energy source. LEDs are usually connected to a driver circuit (usually an integrated circuit) that is configured to supply the LED with energy, i.e. with an electric current. In some embodiments, each light source may comprise a corresponding driver circuit. Alternatively, a common driver circuit may be used to supply (all of) the LEDs with energy. In any case, the driver circuit may be used to drive the LEDs at full intensity. Alternatively or additionally, the driver may be capable of driving the LEDs with less than full intensity, which is denoted "dimming". In general, in illumination systems for microscopes, different levels of light intensity may be desired, so the light sources may be dimmable, i.e. a driver circuit of the light sources may be capable of driving the LEDs with less than full intensity, e.g. in response to a control signal from a control device. Various approaches may be used for the dimming, such as electric current-based dimming, or pulse-width modulation-based dimming. For example, the system 190, e.g. one or more processors 194 of the system 190, shown in FIG. 1c, may be configured to control the light sources. As individual light sources are being used, the light sources may be controlled independently from each other (if each light source has their own driver circuit), or at least in groups (e.g. if the first and second light sources have different driver circuits, or are independently controllable via a single driver circuit). Accordingly, the one or more processors 194 (or, more generally, the system 190) may be configured to control the one or more first and the one or more second LED-based light sources independent from each other.

The illumination system comprises different groups (or sets) of light sources. For example, the illumination system comprises a first group or set of light sources comprising the one or more first LED-based light sources 181-1, and a second group or set of light sources comprising the one or more second LED-based light sources 182. In some embodiments, as also shown in FIGS. 1b, 2a and 2b, the illumination system may even comprise a third group or set of light sources comprising one or more third LED-based light sources 183.

In general, the light sources (or groups/sets) of light sources may be distinguished by the light spectra they emit, or by the light spectra they emit after being filtered by one of the filters. For example, the one or more first LED-based light sources are configured to emit radiation power across the white light color spectrum. In other words, the one or more first LED-based light sources may be configured to emit radiation power at a continuous wavelength band that continually spans at least 90% of the wavelength band between 380 nm and 740 nm. The one or more first LED-based light sources may be broad-band light sources emitting light in a continuous wavelength band spanning at least a 300 nm range. In more generic terms, the one or more first LED-based light sources may be denoted "white light" LEDs, i.e. LEDs that emit radiation power that is perceived as being "white light" due to the inclusion of a wide wavelength band.

The one or more second LED-based light sources are different—they emit radiation power having at least one peak at a wavelength that is tuned to an excitation wavelength of at least one fluorescent material. Accordingly, the one or more second LED-based light sources may be denoted "fluorescence excitation light sources". In other words, the one or more second LED-based light sources may be narrow-band light sources (i.e. they emit at one or multiple wavelength bands each spanning less than a 100 nm wavelength range). This may be achieved using different approaches. For example, the light sources may be light sources that only emit radiation power in a narrow band, without using a filter. In other words, at least a subset of the one or more second LED-based light sources may be configured to provide light having at least one peak at a wavelength that is tuned to an excitation wavelength of the at least one fluorescent material without using a filter to limit the emitted light to the at least one peak. In other words, at least a subset of the one or more second LED-based light sources may comprise LEDs that are configured to emit radiation power in a narrow band (i.e. less than a 100 nm wavelength range, or less than a 50 nm wavelength range). Alternatively or additionally, filters may be used with a subset of the one or more second LED-based light sources. In other words, as further shown in FIGS. 2a and 2b, the illumination system (e.g. at least a subset of the one or more second LED-based light sources) may comprise a second optical filter 184 (e.g. at least one second optical filter 184), arranged to filter the light emitted by at least a subset of the one or more second LED-based light sources. For example, the second filter may be configured to limit the light emitted by at least a subset of the one or more second LED-based light sources to the at least one peak at a wavelength that is tuned to an excitation wavelength of the at least one fluorescent material. In some embodiments, the two approaches may be combined—for a subset of the fluorescent materials, a light source without a filter may be used (as a sufficiently narrow-band light source is available), for another subset of the fluorescent materials, a filter may be used to (further) limit the emitted wavelengths. For example, In the context of this application, the term "light having at least one peak at a wavelength that is tuned to an excitation wavelength of at least one fluorescent material" may be understood as the light having its highest intensity at a wavelength or wavelength band that intersects with an excitation wavelength or wavelength band of at least one fluorescent material, with light at other wavelengths being emitted at an intensity that is at most 80% (or at most 50%, at most 20%, at most 10%) of the highest intensity.

In general, the light emitted by the one or more second LED-based light sources is tuned to the excitation wavelength/wavelengths of at least one fluorescent material. Fluorescent materials are often used in microscopy to highlight a portion of a tissue or a blood vessel that has been previously marked using a fluorescent material. For example, a fluorescent dye, such as fluorescein, indocyanine green (ICG) or 5-ALA (5-aminolevulinic acid) may be used to mark the tissue or vessel. In other words, the at least one fluorescent material may be at least one fluorescent dye. Fluorescent materials are materials that are excited by light at one wavelength/in a first wavelength band (i.e. their "excitation wavelength"), but emit radiation power in another wavelength band (i.e. their "emission wavelength"). Thus, the one or more second LED-based light sources emit radiation power that has its peak at the excitation wavelength/wavelengths of the fluorescent materials. For typically used fluorescent dyes, the excitation wavelength may be between 390 nm and 420 nm, between 460 nm and 500 nm, or between 780 nm and 810 nm. For example, in an example shown in FIGS. 2a and 2b, three different second LED-based light sources are used, having their respective peaks at 405 nm, 480 nm and 788 nm. Accordingly, the one or more second LED-based light sources may be configured to emit radiation power having a peak at one or more of between 390 nm and 420 nm, between 460 nm and 500 nm, and between 780 nm and 810 nm. For example, different light sources of the one or more second LED-based light sources may emit radiation power having a peak at different excitation wavelength/wavelengths of different fluorescent materials. In this case, these different light sources may be controlled mutually independently from each other by the system 190/one or more processors 194.

Figure 2C:
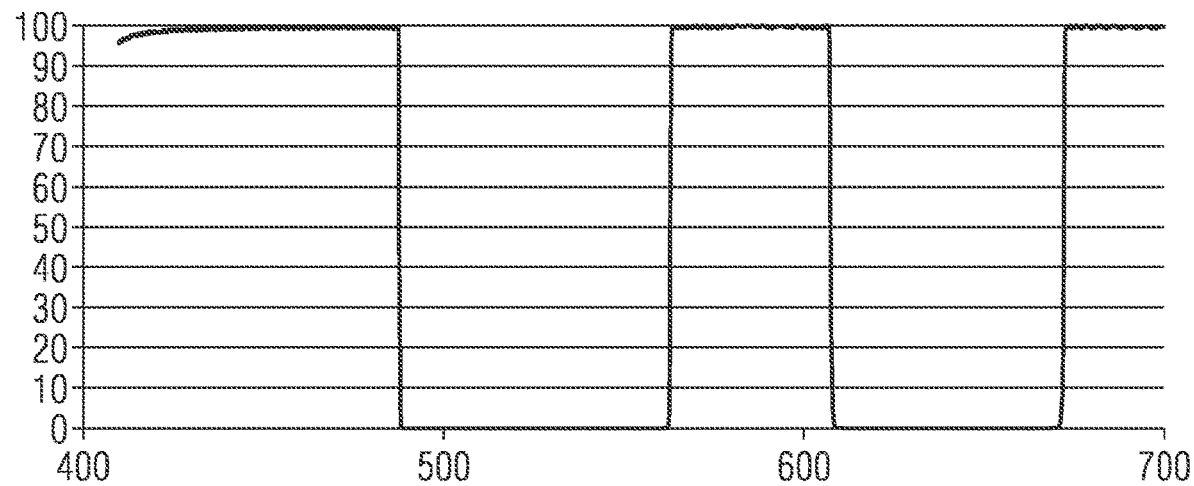
FIG. 2c shows a diagram of a transmission of a band pass filter for filtering white light.

To avoid the one or more first LED-based light sources drowning out the light emitted by the fluorescent materials, light in the emission wavelength bands of the at least one fluorescent material may be filtered out from the light emitted by the one or more LED-based light sources. In other words, the at least one optical filter may be configured to attenuate or block light having a wavelength (spectrum) that coincides with at least one fluorescence emission wavelength (spectrum) of the at least one fluorescent material. Accordingly, the at least one optical filter may be configured to attenuate or block light within at least one of the following wavelength bands: between 490 nm and 560 nm, between 610 nm and 660 nm, and between 750 and 1000 nm. The wavelength bands between 490 nm and 560 nm, between 610 and 660 nm, and between 750 and 1000 nm may be emission wavelength bands of common fluorescent dyes (Fluorescein, 5-ALA and ICG, respectively). In consequence, the first and second sets of light sources may be used concurrently, and the fluorescence emissions may still be visible, as the corresponding portions of the light emitted by the first group or set is filtered out. Accordingly, the at least one optical filter may be arranged in a light path between the one or more first LED-based light sources and a sample to be perceived through the microscope. Furthermore, the at least one optical filter may be arranged to filter the light emitted by each of the one or more first LED-based light sources, i.e. none of the light emitted by the one or more first lights sources may bypass the at least one optical filter. For example, the at least one optical filter may be a bandpass filter, e.g. a bandpass filter with filter characteristics as shown in FIG. 2c. Alternatively, the at least one optical filter may comprise multiple bandpass filters, one for each of the following wavelength bands: between 490 nm and 560 nm, between 610 nm and 660 nm, and between 750 and 1000 nm. One or more of the above-referenced bandpass filters may be used (or combined), depending on which fluorophore is being used. This can be achieved by e.g. by using a filter wheel, or by arranging different bandpass filters in front of different first LED light sources.

In some embodiments, as further shown in FIG. 1b, a third set or group LED-based light sources 183 may be used. In other words, the illumination system 180 may comprise one or more third LED-based light sources 183. The one or more third LED-based light sources may be configured to emit radiation power across the white light color spectrum. Accordingly, the one or more third LED-based light sources may be implemented similar to the one or more first LED-based light sources. The light emitted by third set or group LED-based light sources, however, might not be filtered by the at least one optical filter. Consequently, light emitted by the one or more third LED-based light sources may reach the sample across the (entire) white light color spectrum.

Using the first or third LED-based light sources, two different types of "white light" illumination can be provided—one with portions of the spectrum that are filtered to allow for fluorescence imaging, and one covering the entire spectrum. These two types of "white light" illumination may be used in different modes of operation of the LED-based illumination system. For example, the LED-based illumination system may have two or more modes of operation, one that is suitable for simultaneous reflectance and fluorescence imaging, and one that is only suitable for reflectance imaging. Accordingly, the LED-based illumination system may be configured to, in a first mode of operation, emit the radiation power having at least one peak at a wavelength that is tuned to the excitation wavelength of at least one fluorescent material and the radiation power across the white light spectrum, with the light emitted across the white light spectrum being filtered such that light having a wavelength that coincides with the at least one fluorescence emission wavelength of the at least one fluorescent material is attenuated or blocked. The LED-based illumination system may be configured to, in a second mode of operation, to emit radiation power across the white light spectrum without light having a wavelength that coincides with the at least one fluorescence emission wavelength of the at least one fluorescent material being attenuated or blocked. For example, the first mode of operation may be used for simultaneous reflectance and fluorescence imaging, and the second mode of operation may be used (only or exclusively) for reflectance imaging. For example, the first and second modes of operation may be mutually exclusive.

Figures 1, 6A:
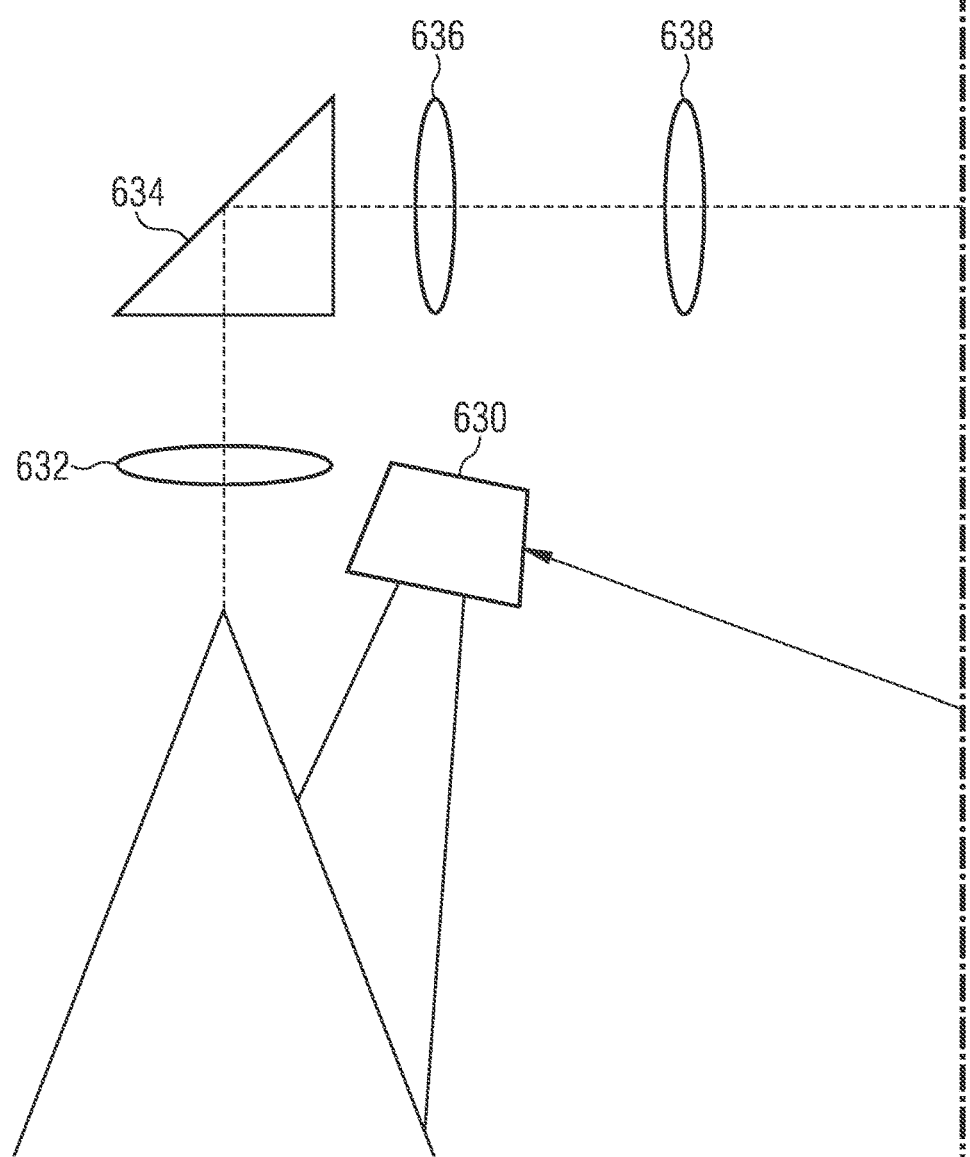
FIGS. 6a to 6d illustrate different illumination modes and imaging modes for an exemplary implementation of a microscope system.
Figures 2, 6A:
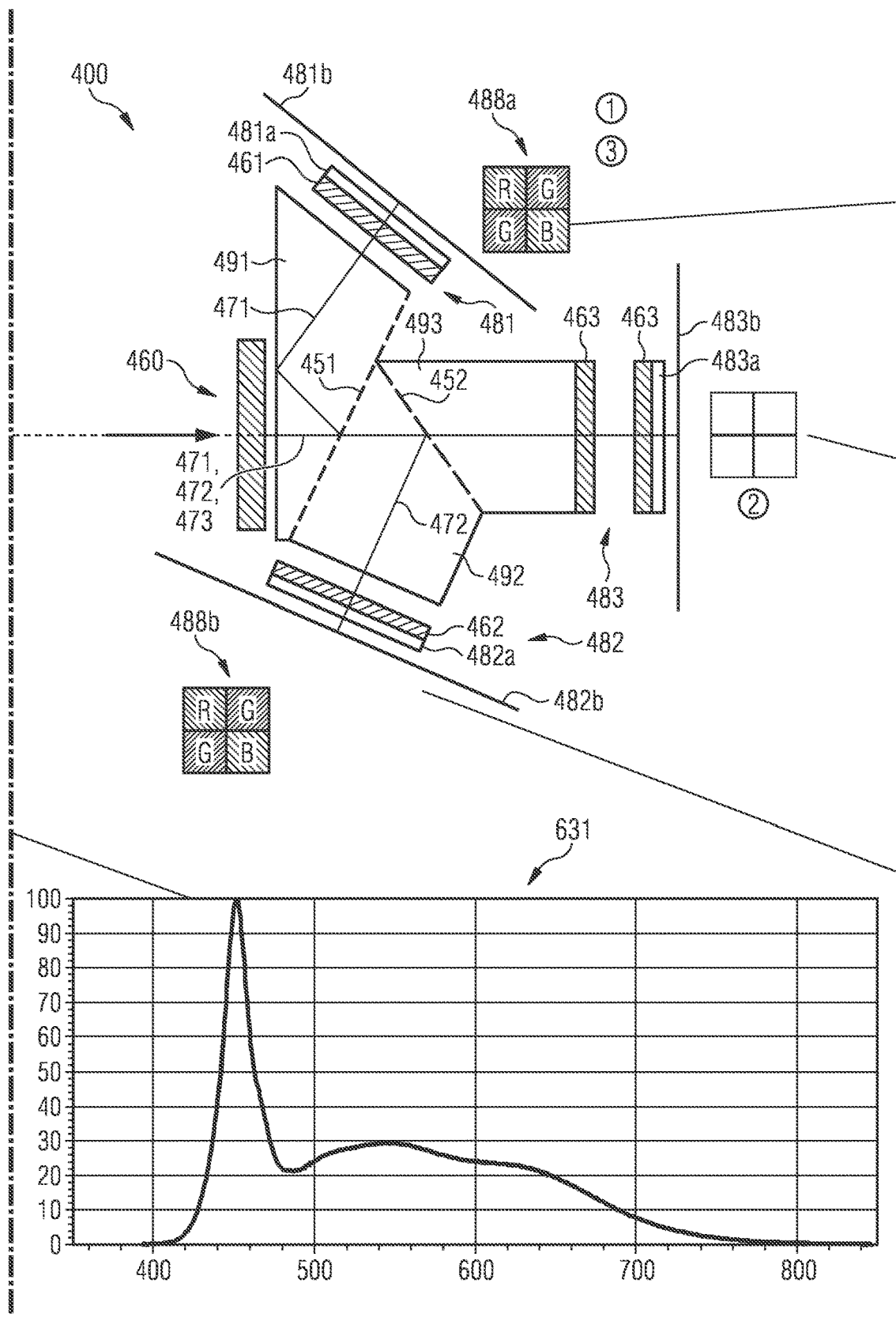
Figures 3, 6A:
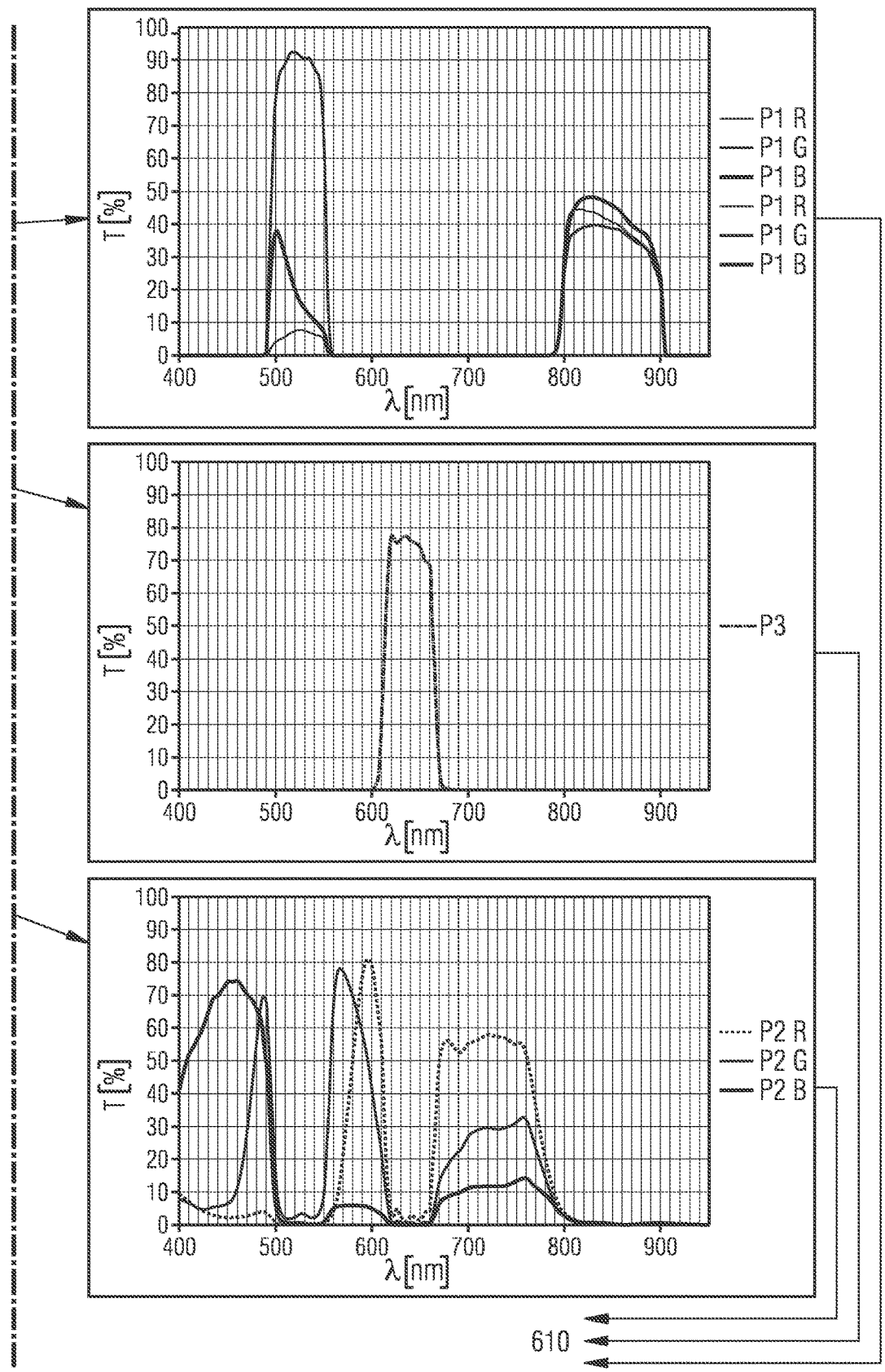
Figures 1, 6B:
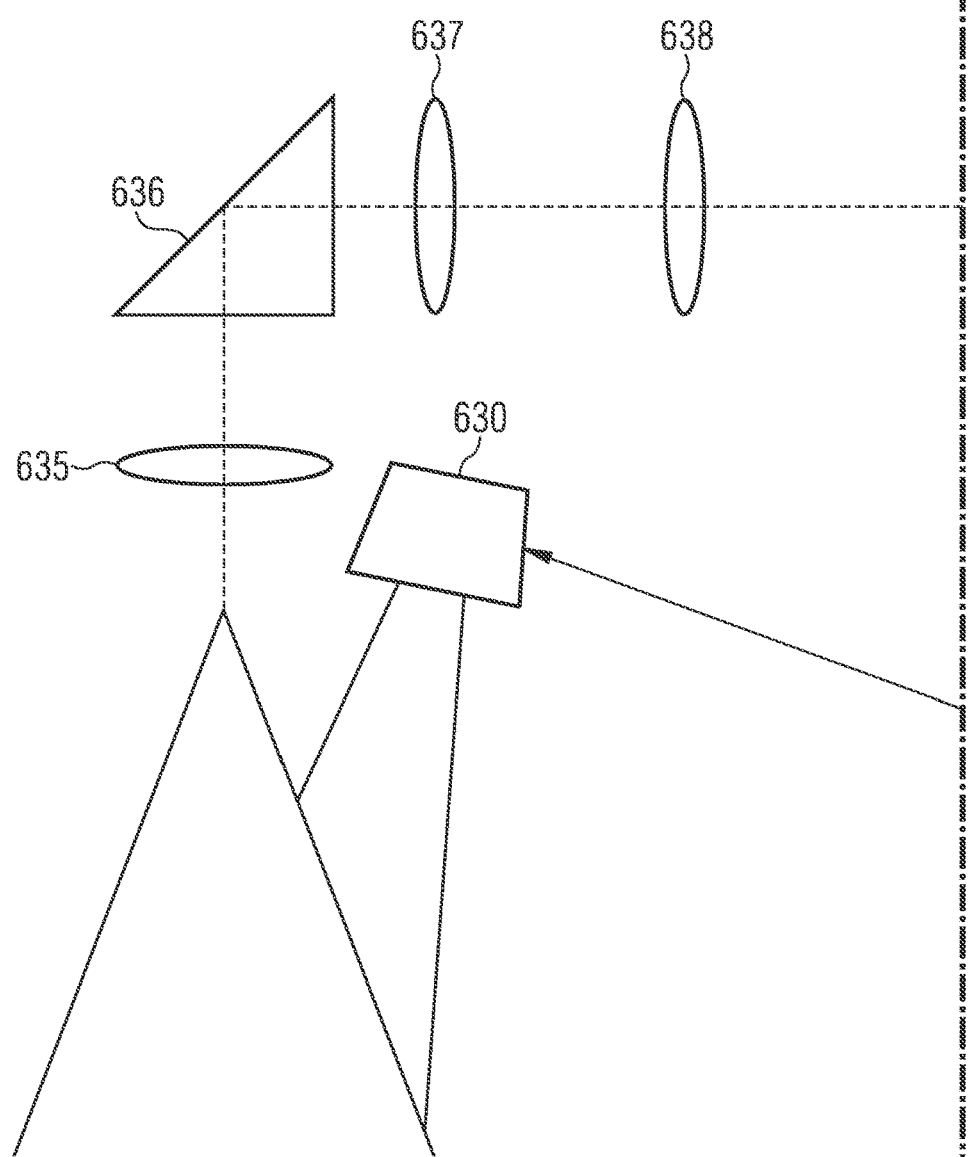
Figures 2, 6B:
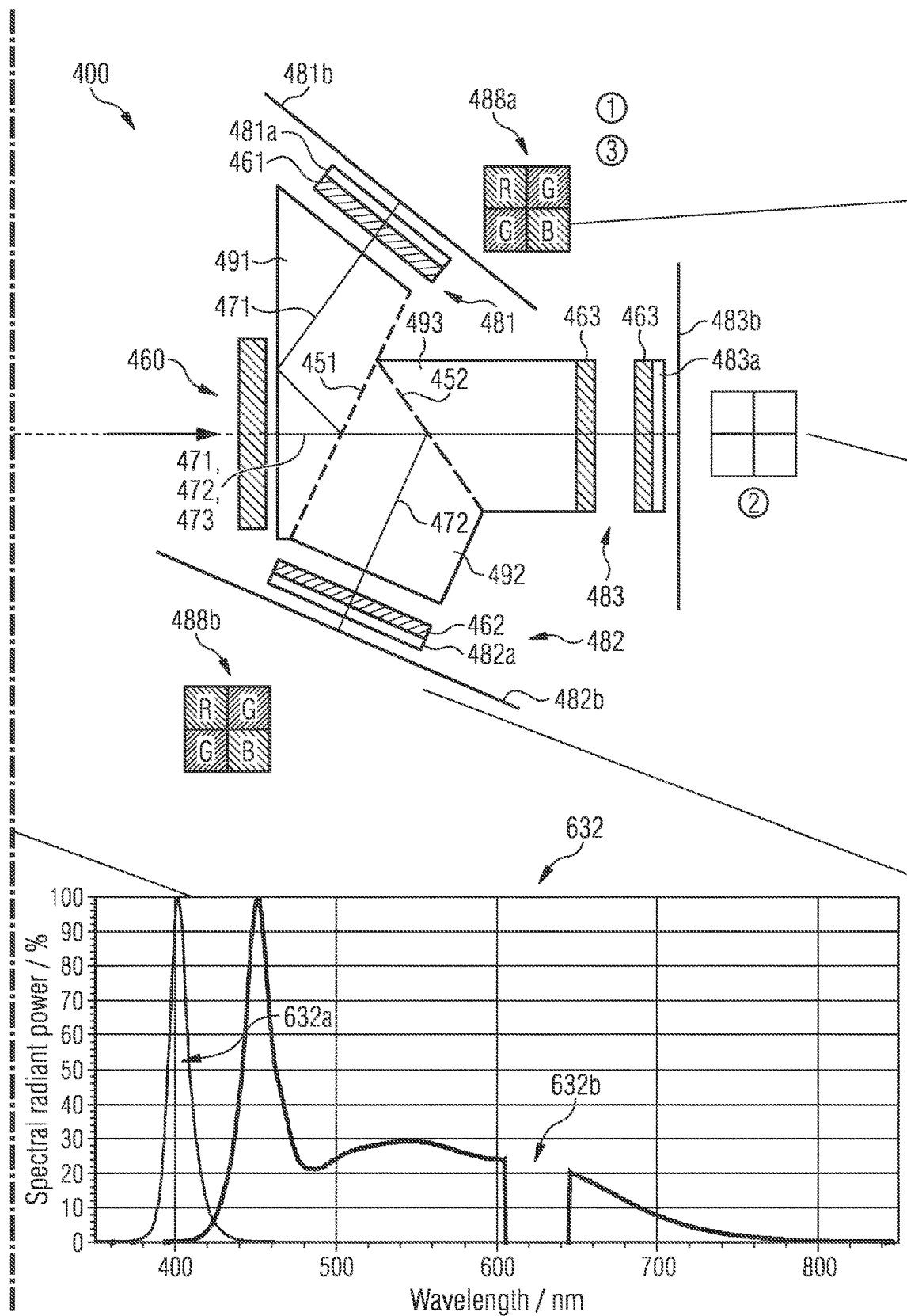
Figures 3, 6B:
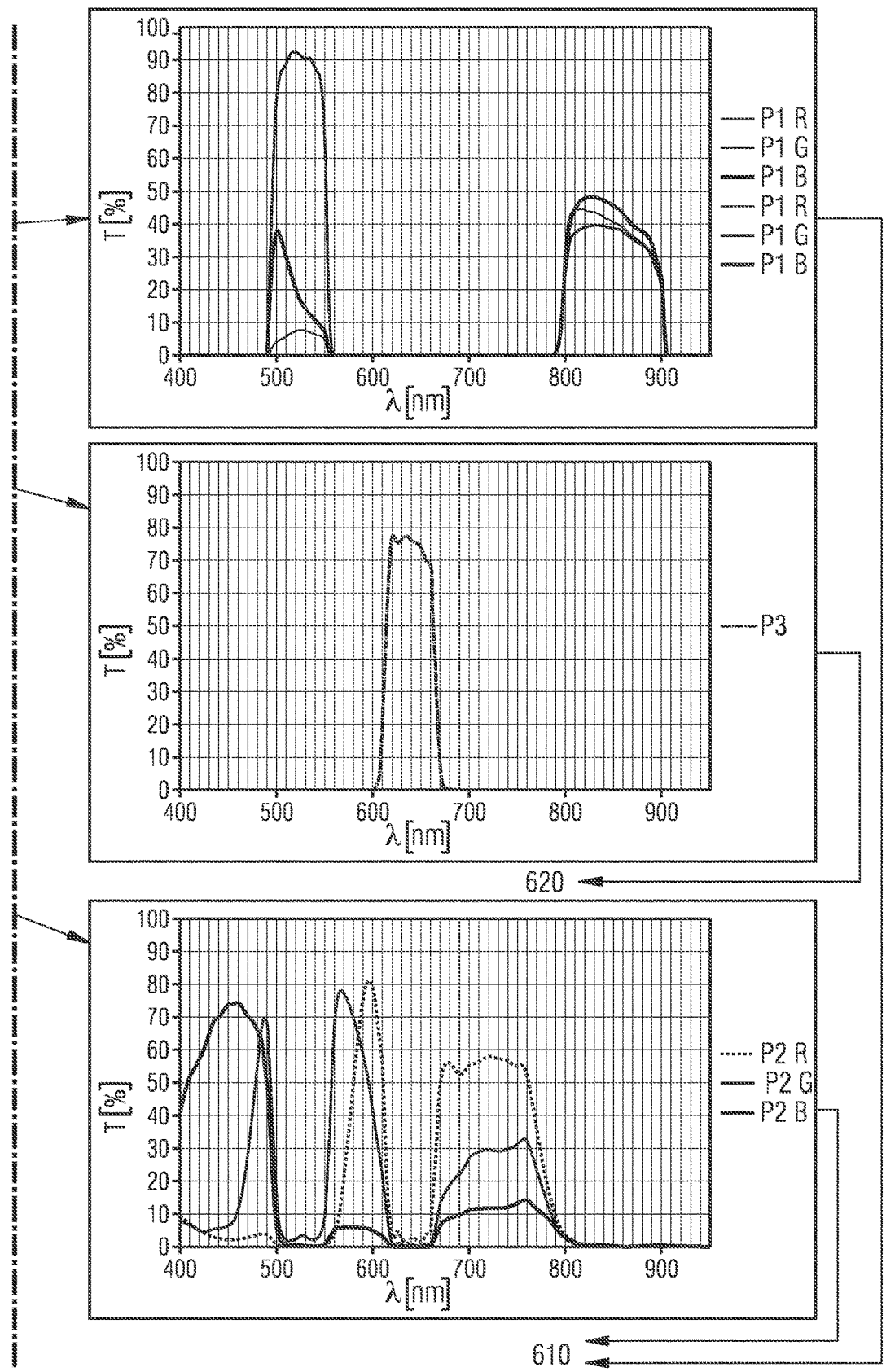
Figures 1, 6C:
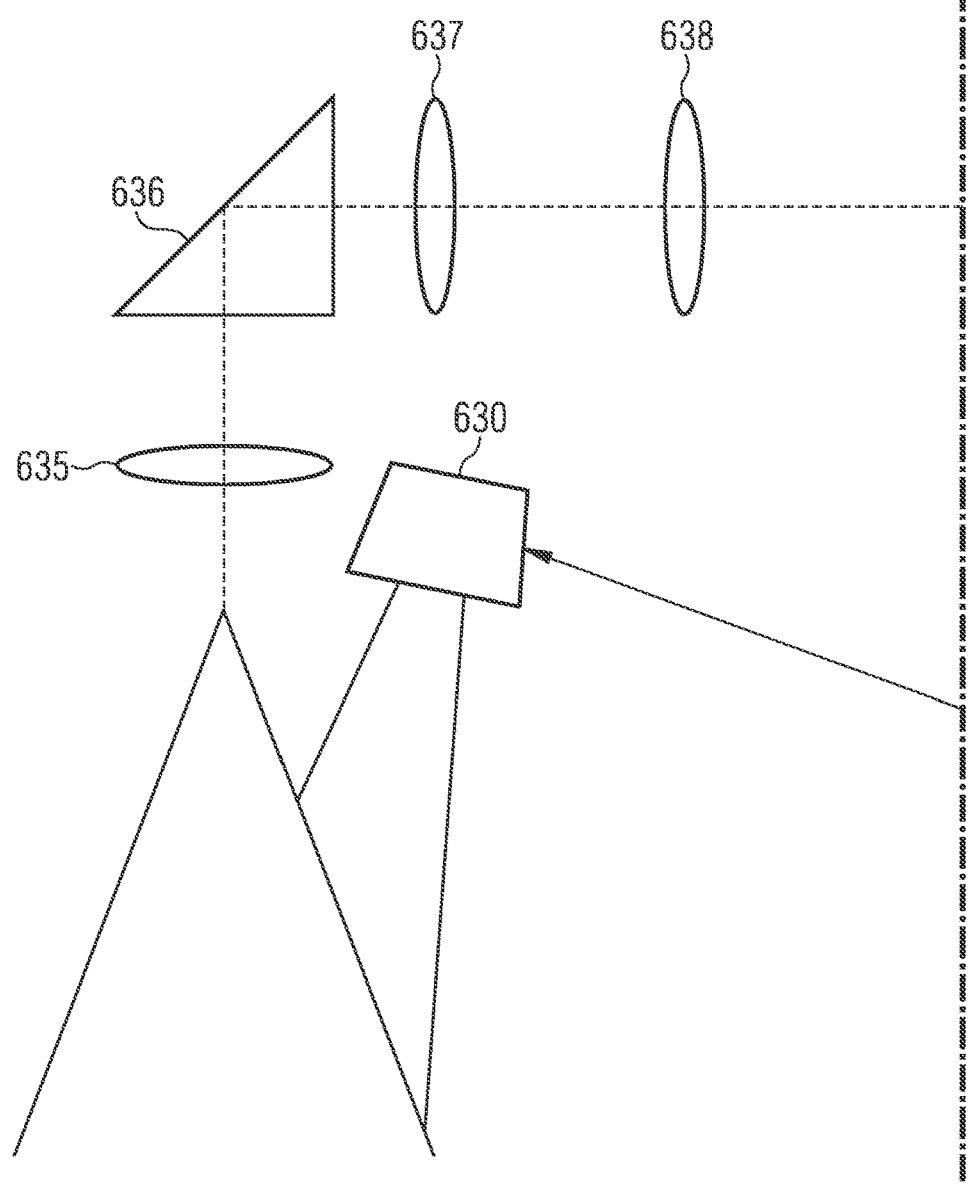
Figures 2, 6C:
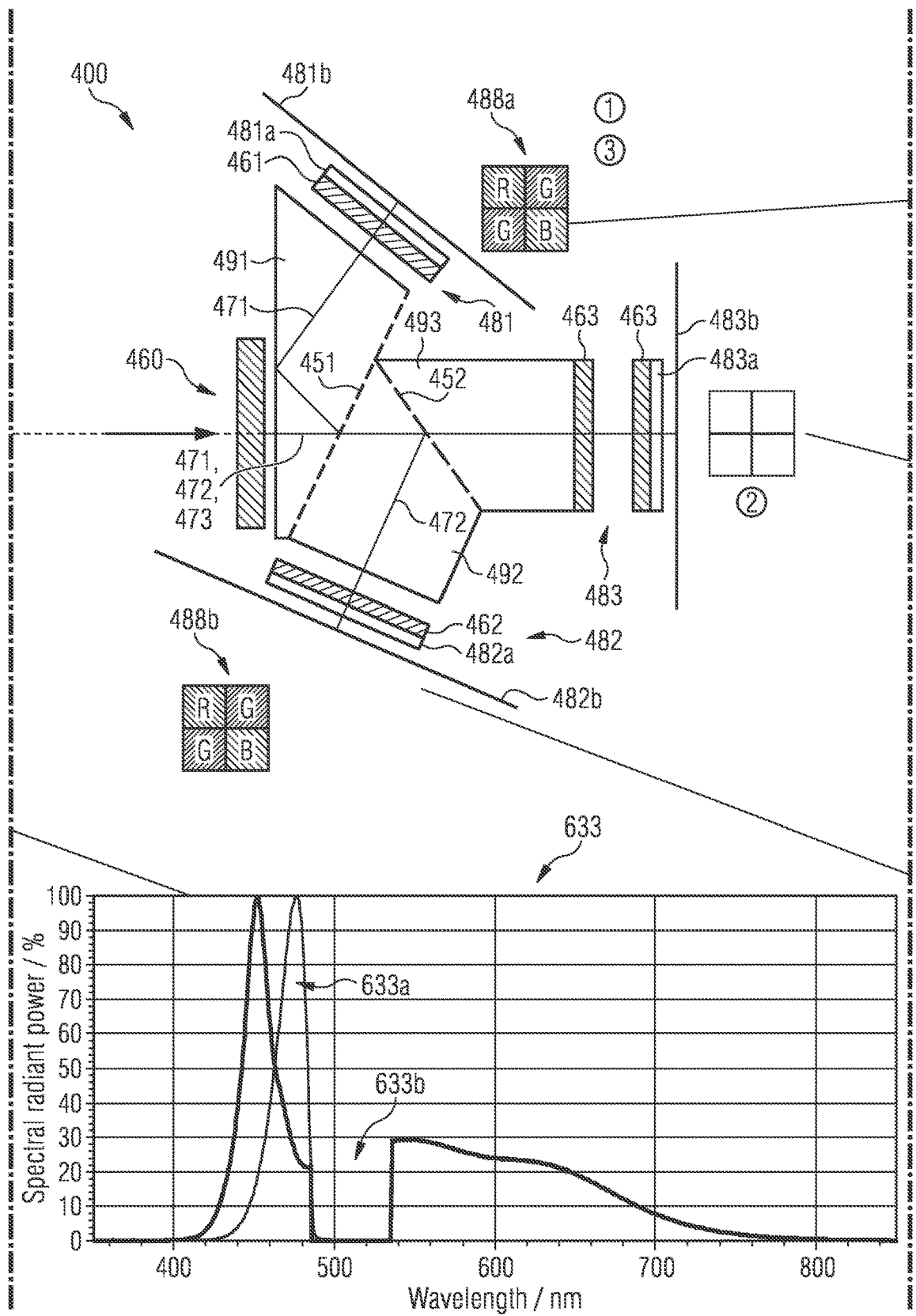
Figures 3, 6C:
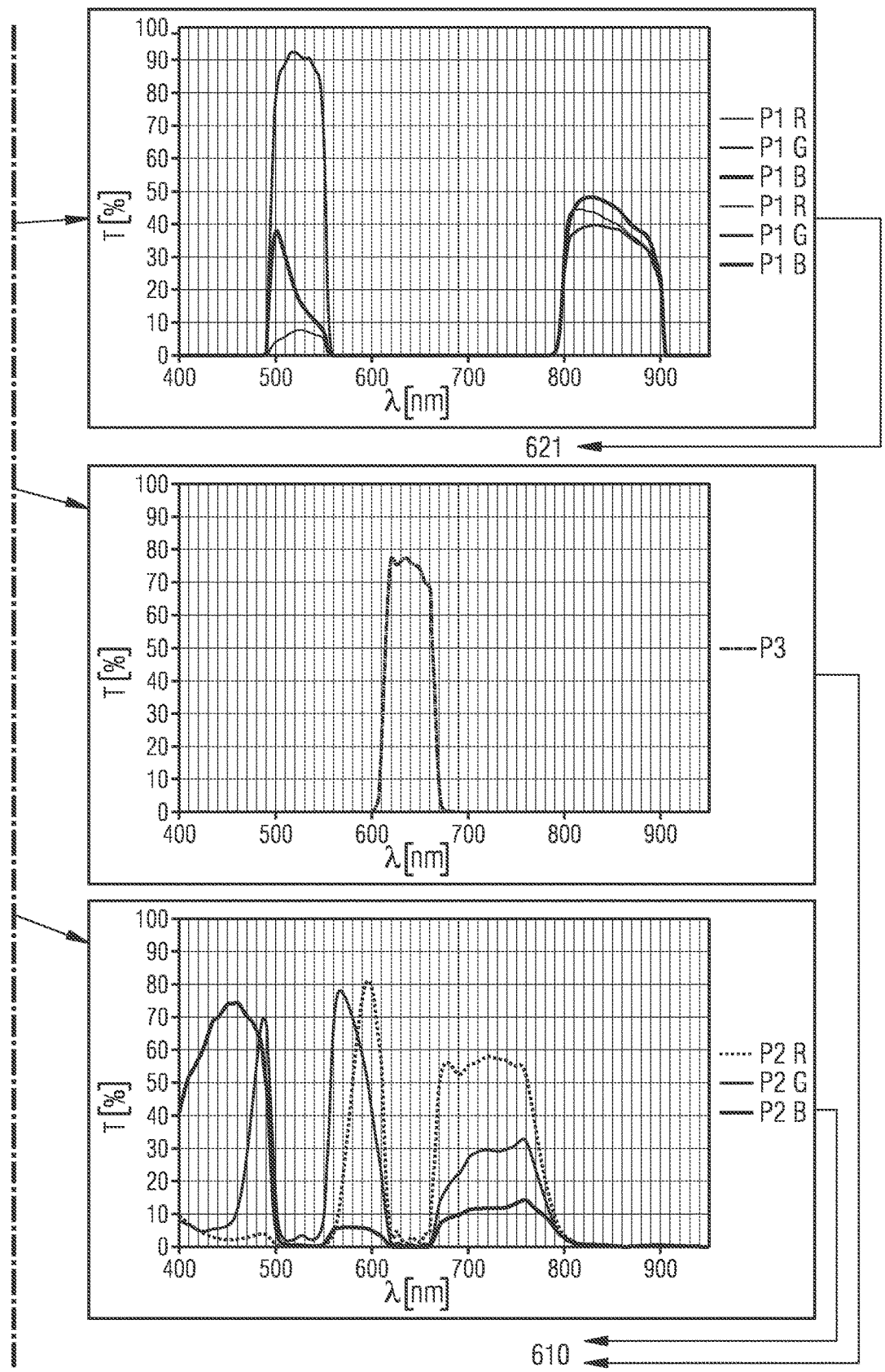

In FIGS. 6a to 6c, illumination spectra 631-634 are shown, which may be generated using the third LED-based light sources (FIG. 6a 631), or a combination of the first and second LED-based light sources (FIGS. 6a to 6c 632-634).

To achieve redundancy and an even illumination of the sample, multiple light sources of each of the groups or sets light sources may be included in the illumination system. For example, the illumination system may comprise two or more first LED-based light sources and two or more second LED-based light sources (and, optionally, two or more third LED-based light sources). In some embodiments, even higher numbers may be used, e.g. four or six first LED-based light sources, four or six first LED-based light sources, and/or four or six third LED-based light sources. In FIGS. 2a and 2b, an example is shown where two first LED-based light sources, six second LED-based light sources and two third LED-based light sources are used.

The light sources of each group or set may be arranged at either side of an objective 102 of the microscope. For example, at least one LED-based light source for each wavelength band (e.g. one first LED-based light source, one third LED-based light source, and three second LED-based light sources for three excitation wavelengths of three fluorescent materials, as shown in FIGS. 2a and 2b) may be arranged at either side of the objective. In other words, at least one of the two or more first LED-based light sources and at least one of the two or more second LED-based light sources (and optionally at least one of the two or more third LED-based light sources) may be arranged at a first side of the objective, and at least one of the two or more first LED-based light sources and at least one of the two or more second LED-based light sources (and optionally at least one of the two or more third LED-based light sources) may be arranged at a second side of the objective. For example, the first side and the second side may be opposing sides relative to the objective of the microscope.

The filters being employed with the one or more first LED-based light sources lead to an illumination of the sample (e.g. of the surgical site) that is non-uniform across the white-light spectrum. This non-uniformity may be compensated in image-processing, e.g. by the system 190.

The microscope system, and in particular the microscope 100, comprises the at least one image sensor assembly 130 configured to generate image data. For example, the one or more processors, or in more general terms the system 190, is configured to obtain image the data of the at least one image sensor assembly 130. Accordingly, the system 190 may be coupled to the microscope, e.g. via the interface 192. For example, the at least one image sensor assembly may correspond to, or comprise, an optical imaging sensor, or multiple optical imaging sensors, as will become evident in the following.

The image data represents at least light reflected by a sample that is illuminated by the LED-based illumination system, e.g. in case reflectance imaging or in case reflectance imaging and fluorescence imaging is performed. In the latter case, the image data represents the light reflected by the sample that is illuminated by the LED-based illumination system and light emitted by the at least one fluorescent material. As will be shown in the following, the image data may comprise different portions that originate from different image sensors of the at least one image sensor assembly. For example, if each image sensor assembly comprises three image sensors, as shown in FIG. 1c and FIGS. 4a to 6d, the image data may comprise three portions originating from the respective sensors. If the image data is stereoscopic image data, and the microscope system comprises two image sensor assemblies, the image data may comprise three portions of image data for each side of the stereoscopic view.

In other words, the microscope system, and in particular the microscope, may comprise comprising two image sensor assemblies.

As has been mentioned above, the at least one image sensor assembly, or each image sensor assembly, may comprise a single image sensor that is used for both reflectance imaging and fluorescence imaging. In some examples, however, a more complex, three sensor setup is used, as illustrated in connection with FIG. 1c and FIGS. 4a to 6d.

FIG. 1c shows a schematic diagram of an example of an image sensor assembly for a microscope. The image sensor assembly of FIG. 1c comprises a beam-splitter assembly 132, 132-1-132-5 and three image sensors 134-1, 134-2, 134-3. The beam-splitter assembly is configured to guide light of a first spectral portion to the first image sensor, light of a second spectral portion to the second image sensor and light of a third spectral portion to the third image sensor. The three image sensors are configured to generate image data based on the spectral portions that are incident to the respective image sensors. Accordingly, the image data may comprise a first portion originating from the first image sensor, a second portion originating from the second image sensor, and a third portion originating from the third image sensor. The three portions of the image data may be contained separately from each other in the image data. A more detailed illustration of a suitable beam-splitter assembly is given in connection with FIGS. 4a to 6d, which illustrate various other components of the image sensor assembly and in particular of the means being used to split the spectrum into the first, second and third spectral portions. In particular, polychroic beam splitters and bandpass filters may be used to separate the spectral portions being guided to the respective image sensors.

In particular, as shown in FIG. 1c, the beam-splitter assembly may comprise three prisms 132-3, 132-4, 132-5 (491, 492, 493 in FIGS. 4a and 4d), with the respective light beams being split (in a wavelength-selective manner) at the beam-splitting coatings 132-1, 132-2 (494, 495 in FIGS. 4a and 4d) being arranged between the respective prisms. For example, the wavelength-selective beam-splitting coatings 132-1, 132-2 may be configured to reflect light having a first spectral characteristic and to admit light having a second spectral characteristic. For example, the first coating 132-1 may be configured to reflect light in the first spectral portion towards the first image sensor 134-1, and to admit the remaining light into the second prism 132-4, where the second coating 132-2 may be configured to reflect light in the second spectral portion towards the second image sensor 134-2, and to admit light in the third spectral portion into the third prism 132-5, where the light is guided towards the third image sensor 134-3. In various examples, bandpass filters may be arranged between the prisms and the respective image sensors, to (only) admit light within the respective spectral portions to be admitted to the respective image sensors. To maintain an equal optical path length for each image sensor (so the captured image is in focus at all image sensors), dummy glass may be arranged between the prisms and the image sensors.

In various examples, the spectrum is subdivided into the three spectral portions. In an ideal scenario, the spectral portions might be non-overlapping, such that light having a given wavelength might only be recorded by (exactly) one of the image sensors. In practice, however, at the edges of the spectral portions, an overlap between the spectral portions may be tolerated.

FIG. 1d shows a schematic diagram of an example of the three spectral portions, showing the first spectral portion 138-1, the second spectral portion 138-2 and the third spectral portion 138-3. As can be seen in FIG. 1d, the first spectral portion may comprise two continuous sub-portions located between 450 nm and 550 nm (comprising a main peak of a fluorescence emission wavelength band of Fluorescein) and between 750 nm and 1000 nm (comprising a main peak of a fluorescence emission wavelength band of Indo-Cyanide Green). Accordingly, at least one of the first and the second spectral portion comprises two spectral subportions spaced apart from each other (i.e. the first, and possibly the second). The third spectral portion may be a continuous portion that is located between 550 nm and 700 nm (comprising a main peak of a fluorescence emission wavelength band of 5-ALA). The second spectral portion 138-2 may comprise the remainder of the spectrum.

In general, image sensors that are used to capture and differentiate light in multiple wavelength bands use pixel-wise color filters, which admit only portions of the spectrum to each pixel. A common type of such color filter is denoted Bayer filter, which comprises, for every 2×2 pixels, two green filters, one red filter and one blue filter. A technique called demosaicing is used in post-processing to determine appropriate color values for each pixel based on the values of the pixel itself and based on the values of its neighbors. In the present disclosure, Bayer filters may be used with at least some of the image sensors, albeit with a post-processing step that is tailored to the illumination and the wavelength bands being used for reflectance and fluorescence imaging. For example, as shown in FIG. 1c, a first (134-1) and a second (134-2) of the three image sensors are operated with Bayer filters 136-1, 136-2, and a third of the three image sensors is operated without a Bayer filter.

For example, the image sensor or image sensors may comprise or be APS (Active Pixel Sensor)—or a CCD (Charge-Coupled-Device)-based imaging sensors. For example, in APS-based image sensors, light is recorded at each pixel using a photo-detector and an active amplifier of the pixel. APS-based image sensors are often based on CMOS (Complementary Metal-Oxide-Semiconductor) or S-CMOS (Scientific CMOS) technology. In CCD-based image sensors, incoming photons are converted into electron charges at a semiconductor-oxide interface, which are subsequently moved between capacitive bins in the imaging sensors by a control circuitry of the imaging sensors to perform the imaging. The system, i.e. the one or more processors, may be configured to obtain (i.e. receive or read out) the image data from the respective image sensor(s) of the at least one image sensor assembly. The image data may be obtained by receiving the image data from the image sensor(s) (e.g. via the interface 192), by reading the image data out from a memory of the image (e.g. via the interface 192), or by reading the image data from a storage device 196 of the system 190, e.g. after the image data has been written to the storage device 196 by the image sensor(s) or by another system or processor.

The system 190, and in particular the one or more processors 194, is/are configured to process the image data to generate processed image data. In general, the system 190 may be used with any illumination system for a microscope that is configured to provide light that is filtered such that light having a wavelength (spectrum) that coincides with at least one fluorescence emission wavelength (spectrum) of the at least one fluorescent material is attenuated or blocked. In particular, however, the light may be provided by the illumination system 180 shown in FIG. 1b. In this case, the image data may represent light reflected by the sample that is illuminated by the one or more first LED-based light sources 181-1 of the illumination system 180. The filtering of the light has the effect, that reflections of the respective portions of the white light spectrum are not (or to a lesser degree, in case of attenuation) represented by the image data.

The image data at least represents light reflected by a sample that is illuminated by one or more LED-based light sources (e.g. by the one or more first LED-based light sources 181-1 of FIG. 1*a*). The light emitted by the one or more LED-based light sources is filtered such that light having a wavelength (spectrum) that coincides with at least one fluorescence emission wavelength (spectrum) of the at least one fluorescent material is attenuated or blocked (e.g. by the at least one optical filter 181-2). Additionally, the image data may represent light emitted at the at least one fluorescence emission wavelength spectrum by at least one fluorophore.

The system is configured to process the image data to generate processed image data. In other words, the system may be configured to perform image processing on the image data. For example, the image processing may be performed to compensate for (or reduce the effects of) the non-uniformity of the illumination over the white light spectrum. For example, the system may be configured to reconstruct the portion of the processed image data representing light having a wavelength spectrum that coincides with the at least one fluorescence emission wavelength spectrum of the at least one fluorescent material, e.g. by using information from adjacent wavelength bands. For example, if light in one of the wavelength bands between 490 nm and 560 nm, and between 610 and 660 nm is blocked or attenuated in the illumination of the sample, light from adjacent wavelength bands (e.g. up to 490 nm, between 560 nm and 610 nm, and from 660 nm up) may be used to reconstruct the light that has been blocked or attenuated by the filter. In other words, the system may be configured to reconstruct the light that is attenuated or blocked, i.e. the light having a wavelength spectrum that coincides with at least one fluorescence emission wavelength spectrum of the at least one fluorescent material. For example, the system may be configured to apply a transformation function that performs a transformation between the image data (which may be raw image data, i.e. comprise the sensor output of the optical imaging sensor) and the processed image data, with the transformation function mapping the wavelength bands outside the at least one fluorescence emission wavelength to the (entire) white light spectrum. Thus, a portion of the processed image data representing light having a wavelength spectrum that coincides with the at least one fluorescence emission wavelength spectrum of the at least one fluorescent material is generated (i.e. reconstructed) based on the image data.

Additionally, the image processing may be performed to generate an overlay representing fluorescence emissions, which may be overlaid over the white light image within the processed image data. As has been mentioned above, the image data might not only represent the light reflected by the sample that is illuminated by the LED-based illumination system, but also light emitted by the at least one fluorescent material. Accordingly, the system, and in particular the one or more processors, may be configured to generate a first image representing visible light (based on a portion of the image data representing the light reflected by the sample) and a second image representing fluorescence emissions (based on a portion of the image data representing the light emitted by the at least one fluorescent material) of the at least one fluorescent material based on the image data. However, in some scenarios, the user of the microscope might only require reflectance imaging, e.g. if no fluorophores are being used. In this case, the generation of the second image may be omitted. In other words, the LED-based illumination system may have two or more modes of operation, with the first mode of operation being suitable for reflectance imaging and fluorescence imaging, and with and the second mode of generation being suitable for reflectance imaging. The one or more processors may be configured to generate the first image and the second image if the LED-based illumination system operates in the first mode of operation, and to generate the first image without generating the second image if the LED-based illumination system operates in the second mode of operation.

As mentioned above, the image data may comprise three portions that originate from the respective first, second and third image sensors. These portions may be combined, in different ways, to generate the first and second images. In other words, the one or more processors may be configured to generate the first image representing visible light based on a first combination of the three portions of the image data, and to generate the second image representing fluorescence emissions of the at least one fluorescent material based on a second combination of the three portions of the image data.

Figures 1, 6D:
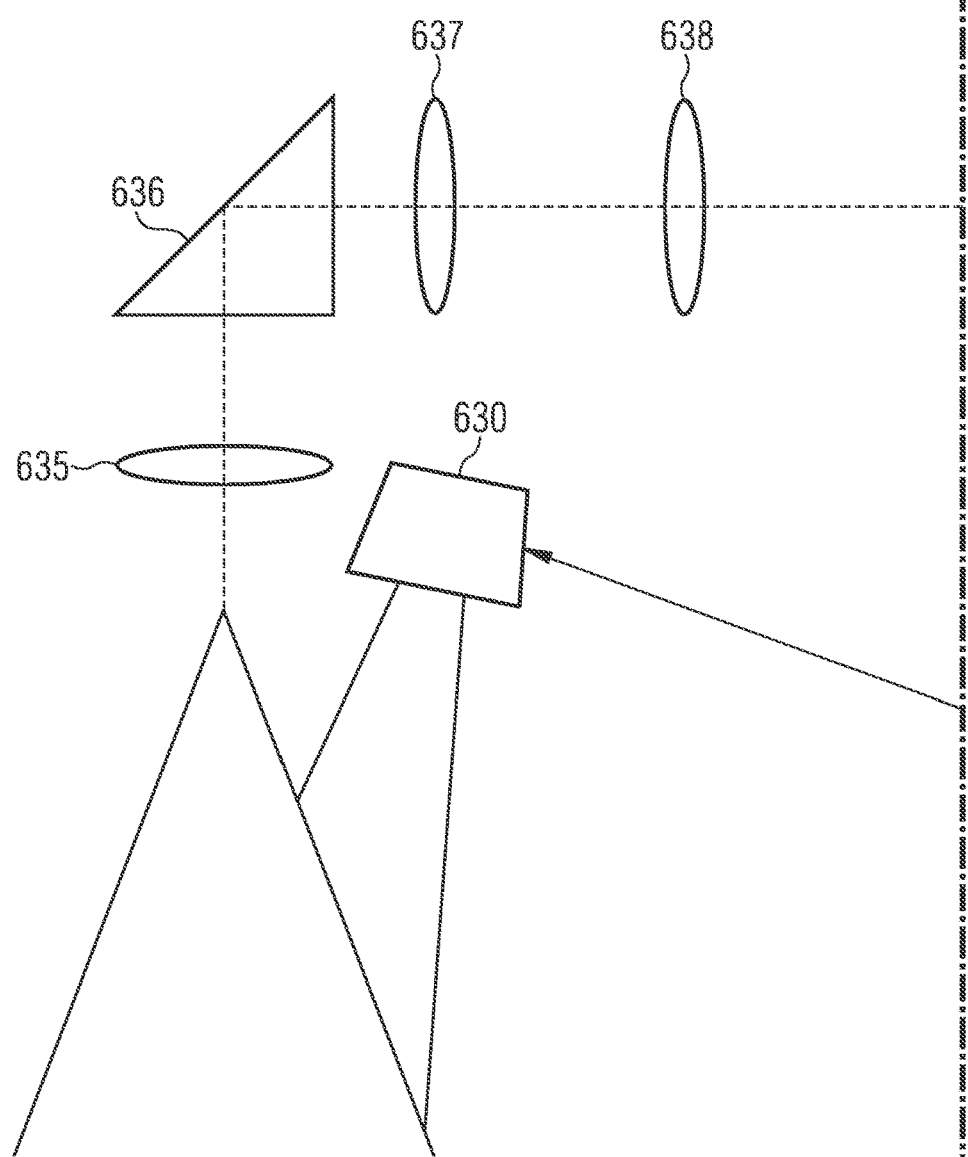
Figures 2, 6D:
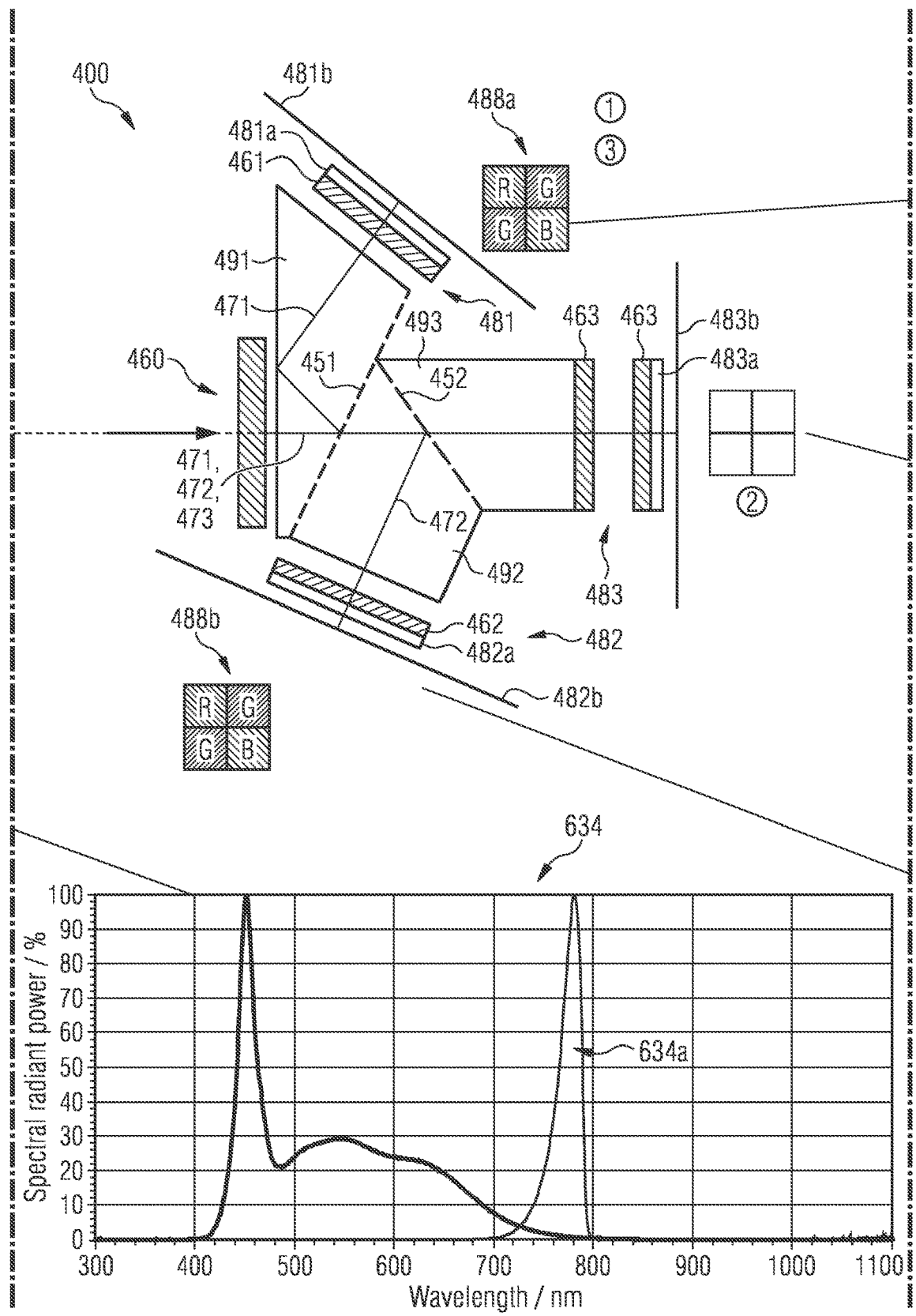
Figures 3, 6D:
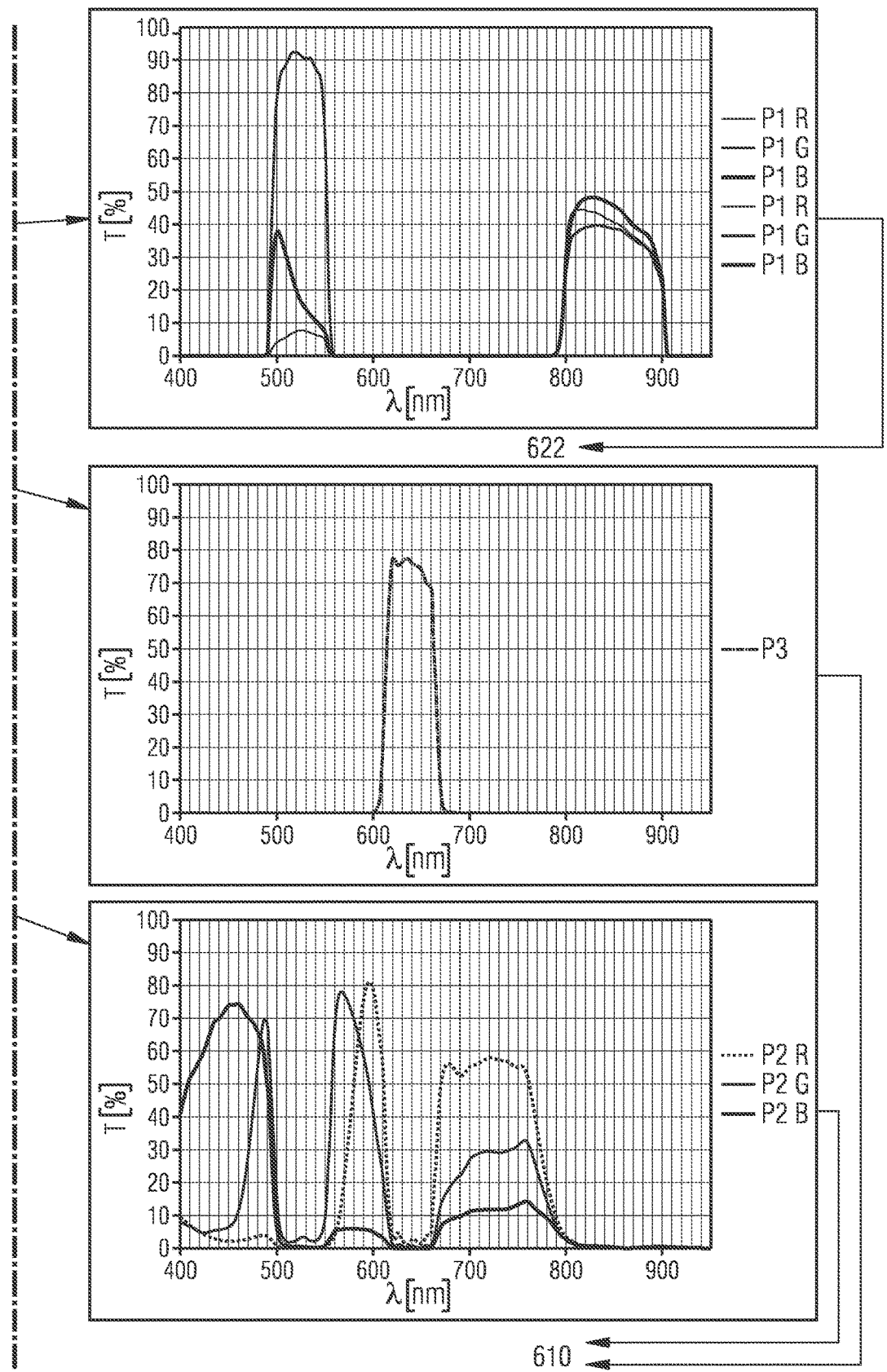

Which portions of the spectrum are being used to generate the first image, and optionally the second image, depends on whether fluorescence imaging is being performed, and on which and how many fluorophores are being used. For example, the one or more processors may be configured to combine the three portions of the image data such that, if light is emitted having (exactly) one peak at a wavelength that is tuned to an excitation wavelength of one fluorescent material, the first image is generated based on (at least) two portions of the image data and the second image is generated based on one portion of the image data. A more detailed illustration is given in FIGS. 6*a* to 6*d*. In FIG. 6*a*, only the first image is generated, based on all three portions of the image data. In FIG. 6*b*, where a fluorophore (5-ALA) with an emission wavelength band having a peak between 600 and 650 nm is being used, the first image is generated based on the first and second portion, and the second image is generated based on the third portion. In FIG. 6*c*, where a fluorophore (Fluorescein) with an emission wavelength band having a peak between 490 and 540 nm is used, the first image is generated based on the second portion and the third portion (and optionally based on the first portion, with the fluorescence emissions being computationally removed), and the second image is generated based on the first portion. In FIG. 6*d*, where a fluorophore (ICG) with an emission wavelength band having a peak between 750 and 1000 nm is used, the first image is generated based on the second portion and the third portion (and optionally based on the first portion, with the fluorescence emissions being computationally removed), and the second image is generated based on the first portion.

However, multiple fluorophores may be used at the same time. For example, three fluorophores may be used at the same time, having emission peaks as described above. If light is emitted having three peaks at three wavelengths that are tuned to excitation wavelengths of three fluorescent materials, the first image may be generated based on one portion of the image data (e.g. the second portion) and the second image is generated based on two portions of the image data (e.g. the first and third portion).

If two fluorophores are being used at the same time, the combination of portions depends on the fluorophores being used. For example, if Fluorescein and ICG are used, the first image may be generated based on the second and third portion, and the second image may be generated based on the first portion. If 5-ALA is used in combination with Fluorescein or ICG, the first image may be generated based on the second portion (and optionally a sub-portion of the first portion outside the fluorescence emission wavelength band of the respective fluorophore), and the second image may be generated based on the third portion (for the 5-ALA) and based on the first portion (for the remaining fluorophore). In other words, the first portion may be indicative of fluorescence emissions by Fluorescein and ICG, and the third portion may be indicative of fluorescence emissions by 5-ALA. The second portion of the image data, on the other hand, might only be used for reflectance imaging. Accordingly, the one or more processors may be configured to generate the first image at least based on the second portion of the image data.

In more abstract terms, depending on the fluorophore or fluorophores being used, different combinations of the portions may be chosen. In other words, the one or more processors may be configured to combine the three portions of the image data such, that, if light is emitted having a peak at a first wavelength that is tuned to an excitation wavelength of a first fluorescent material (e.g. Fluorescein or ICG), the second image is generated based on the first portion of the image data, and such that, if light is emitted having a peak at a second wavelength that is tuned to an excitation wavelength of a second fluorescent material (e.g. ALA), the second image is generated based on the third portion of the image data. The one or more processors may be configured to combine the three portions of the image data such, that, if light is emitted having a peak at a third wavelength (the other of Fluorescein and ICG not being used above) that is tuned to an excitation wavelength of a third fluorescent material, the second image is generated based on the first portion of the image data.

In addition, the system may be used to control the LED-based light sources. Accordingly, the system 190, e.g. the one or more processors 194, may be coupled to the illumination system 180, e.g. via the interface 192. The one or more processors 194 (e.g. the system 190) may be configured to control the one or more first and the one or more second LED-based light sources independent from each other. For example, at least one of an on-off-state and a light intensity may be controlled independently for the one or more first and the one or more second LED-based light sources (and optionally for the one or more third LED-based light sources). More precisely, an on-off-state and/or a light intensity for the one or more first LED-based light sources may be controlled independently from an on-off-state and/or a light intensity for the one or more second LED-based light sources (and optionally from an on-off-state and/or a light intensity for the one or more third LED-based light sources). In some cases, also the properties of the at least one optical filter may be controlled by the system (e.g. via the filter wheel). In some embodiments, each LED-based light source may be controlled independently from each other (or at least independently from LED-based light sources of other groups or sets).

The one or more processors may be configured to provide the processed image data, e.g. comprising the first and (optionally) the second image. For example, a portion of the processed image data representing light having a wavelength that coincides with the at least one fluorescence emission wavelength of the at least one fluorescent material may be generated based on the image data, e.g. by reconstructing the portions of the spectrum that coincide with the at least one fluorescence emission wavelength of the at least one fluorescent material, or by overlaying the respective portions of the second image (representing the respective portions of the spectra) over the first image data. The system, and in particular the one or more processors, may be configured to output the processed image data (e.g. via the interface 192 or via the one or more storage devices 196).

The interface 192 may correspond to one or more inputs and/or outputs for receiving and/or transmitting information, which may be in digital (bit) values according to a specified code, within a module, between modules or between modules of different entities. For example, the interface 192 may comprise interface circuitry configured to receive and/or transmit information. In embodiments the one or more processors 194 may be implemented using one or more processing units, one or more processing devices, any means for processing, such as a processor, a computer or a programmable hardware component being operable with accordingly adapted software. In other words, the described function of the one or more processors 194 may as well be implemented in software, which is then executed on one or more programmable hardware components. Such hardware components may comprise a general-purpose processor, a Digital Signal Processor (DSP), a micro-controller, etc. In at least some embodiments, the one or more storage devices 196 may comprise at least one element of the group of a computer readable storage medium, such as an magnetic or optical storage medium, e.g. a hard disk drive, a flash memory, Floppy-Disk, Random Access Memory (RAM), Programmable Read Only Memory (PROM), Erasable Programmable Read Only Memory (EPROM), an Electronically Erasable Programmable Read Only Memory (EEPROM), or a network storage.

More details and aspects of the microscope system, the microscope, the illumination system, the at least one image sensor assembly and the different spectra are mentioned in connection with the proposed concept or one or more examples described above or below (e.g. FIGS. 2a to 7). The microscope system, the microscope, the illumination system, the at least one image sensor assembly and the different spectra may comprise one or more additional optional features corresponding to one or more aspects of the proposed concept or one or more examples described above or below.

FIGS. 2a and 2b show schematic diagrams of examples of a microscope system. FIGS. 2a and 3a show a placement of LED-based light sources 181-1, 182 and 183 of the illumination system 180 relative to an objective 102 of a microscope. FIG. 2a shows a view of a microscope front, and FIG. 2b shows a sectional view thereof. Each of the LED-based light source of the illumination system is configured to emit light towards a sample to be observed via the microscope, and each LED-based light source is arranged in adjacent to the objective 102 of the microscope. For example, the LED-based light sources may be arranged at (i.e. adjacent to) an entrance of the objective that is directed at the sample to be observed via the microscope, e.g. at a downward-facing entrance of the objective. For example, each LED-based light source may be arranged such, that the light emitted by the light source is emitted at least in parallel to a light path of the microscope that traverses the objective of the microscope. For example, the one or more first and the one or more second (and optionally the one or more third) LED-based light sources may be arranged at a side of the microscope facing towards the sample (also denoted "entrance side") of the microscope.

As has been introduced above, multiple light sources of each of the groups or sets light sources may be included in the illumination system. For example, the illumination system may comprise two or more first LED-based light sources and two or more second LED-based light sources (and, optionally, two or more third LED-based light sources). In FIGS. 2a and 2b, an example is shown where two first LED-based light sources, six second LED-based light sources and two third LED-based light sources are used. The light sources of each group or set may be arranged at either side of an objective 102 of the microscope. For example, the respective sides may be opposing sides relative to the objective 102 of the microscope.

In FIGS. 2a and 2b, the placement of the at least one optical filter 181-1 (in front of the one or more first LED-based light sources) and of the at least one second optical filter 184 (in front of four of the second LED-based light sources at the edges of the array of light sources) is shown. Additionally, in FIG. 2b, the arrangement of the CPCs relative to the LED-based light sources is shown.

As shown in FIGS. 2a and 2b, an (one-dimensional) array of combinations of LED-CPC (LED-based light source plus Compound Parabolic Concentrator) may be placed sideways along the objective. Some LED-CPC combination (i.e. the first LED-based light sources) have a band pass filter (i.e. the at least one optical filter) for a defined control of the emitted spectrum. In the example shown in FIGS. 2a and 2b, Five LED-CPCs are placed on each side of the objective. Two of these LEDs have a spectrum across the visible range (white light LED), i.e. the one or more first LED-based light sources 181-1. One LED emits a spectrum with a peak at 405 nm, one LED with a peak at 480 nm, one LED with a peak at 788 nm (i.e. the one or more second LED-based light sources 116). In front of one of the white light LEDs an additional band pass filter is placed (e.g. the band-pass filter of FIG. 2c), which blocks the fluorescence emissions of two fluorescent materials. Two band pass filters are placed in front of the 480 nm and 788 nm LED.

More details and aspects of the illumination system and microscope system are mentioned in connection with the proposed concept or one or more examples described above or below (e.g. FIG. 1a to 1d, 2c to 7). The illumination system and microscope system may comprise one or more additional optional features corresponding to one or more aspects of the proposed concept or one or more examples described above or below.

FIG. 2c shows a diagram of a transmission of a band pass filter for filtering white light. On the x-axis, the wavelength in nm is shown, on the y-axis, the transmission in % is shown. For example, the shown filter may be used to implement the at least one optical filter 181-2 of FIGS. 1a to 2b. As shown in FIG. 2c, the filter may block or attenuate light in the range between 490 nm and 560 nm, and between 610 nm and 660 nm wavelength.

More details and aspects of the bandpass filter are mentioned in connection with the proposed concept or one or more examples described above or below (e.g. FIG. 1a to 2b, 3 to 7). The bandpass filter may comprise one or more additional optional features corresponding to one or more aspects of the proposed concept or one or more examples described above or below.

Figure 3:
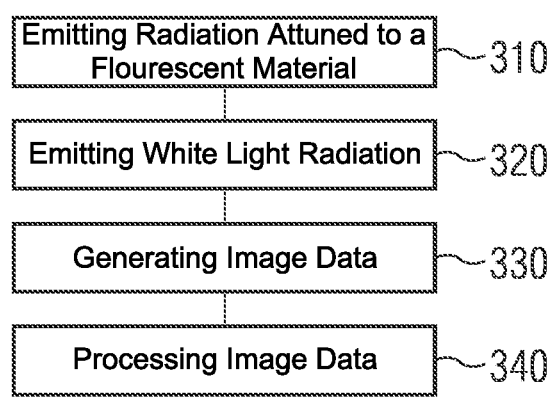
FIG. 3 shows a flow chart of an example of method for imaging an object using a microscope.

FIG. 3 shows a flow chart of an example of method for imaging an object using a microscope. For example, the microscope may correspond to the microscope shown in connection with FIGS. 1a to 2c. Accordingly, the method may be performed by the microscope or microscope system shown in connection with FIGS. 1a to 2c. The method comprises emitting 310, using an LED-based illumination system (such as the LED-based illumination system 180 shown in connection with FIGS. 1a to 1b), e.g. by controlling the LED-based illumination system, radiation power having at least one peak at a wavelength that is tuned to an excitation wavelength of at least one fluorescent material. The method comprises emitting 320, using the LED-based illumination system, e.g. by controlling the LED-based illumination system, radiation power across a white light spectrum. The light emitted across the white light spectrum is filtered such that light having a wavelength spectrum that coincides with at least one fluorescence emission wavelength spectrum of the at least one fluorescent material is attenuated or blocked. In other words, the method may comprise emitting the light emitted across the white light spectrum. The method comprises generating 330 image data, the image data representing light reflected by a sample that is illuminated by the LED-based illumination system. The method comprises processing 340 the image data to generate processed image data.

For example, features introduced in connection with FIGS. 1a to 2c, may likewise be applied to the corresponding method of FIG. 3.

More details and aspects of the method are mentioned in connection with the proposed concept or one or more examples described above or below (e.g. FIG. 1a to 2c, 4a to 7). The method may comprise one or more additional optional features corresponding to one or more aspects of the proposed concept or one or more examples described above or below.

In FIGS. 4a to 4f, a more detailed introduction to an example of the image sensor assembly or image sensor assemblies 130 is given, and in particular a more detailed introduction to an example of the optical beam splitter assembly 132.

Various aspects of the present disclosure relate to an optical beam splitter assembly, a camera head, and a microscope assembly. Optical beam splitter assemblies can be used for example in microscopes, in particular in surgical microscopes when fluorophores are used to mark characteristic tissue.

Various aspects of the present disclosure may use an optical beam splitter assembly for recording images in at least three different spectral portions. The beam splitter assembly may comprise a first and a second beam splitter, and a first, second and third light path. The first light path may be configured to guide light of a first spectral portion from a light entrance section to a first light output section. The second light path may be configured to guide light of a second spectral portion from the light entrance section to a second light output section.

The second light output section may be spaced apart from the first light output section. The third light path may be configured to guide light of a third spectral portion from the light entrance section to a third light output section. The third light output section may be spaced apart from the first light output section and the second light output section. The second light path may traverse the first beam splitter, and the third light path may traverse the first and the second beam splitter. Alternatively, a different optical beam splitter assembly may be used to split the first, second and third spectral portions and direct them from a light entrance portion to three light output sections.

This allows for capture of images in the at least three different spectral portions, such that three fluorescent wavelength bands can be distinguished, and a visible arrangement can be generated. In principle, such an arrangement can be used for all four images (one image for visible light and three images for fluorescence emissions in three different wavelength bands with appropriate illumination. In practice, a first image (or second portion of the image data in the terms used in connection with FIGS. 1a to 1d) representing visible light, a second image (or third portion of the image data) representing light in a first fluorescence emission wavelength band (e.g. at approximately 800 nm) and, and a third image (or a first portion of the image data) representing light in a second fluorescence emission wavelength band (e.g. at approximately 400 nm) or a third fluorescence emission wavelength band (e.g. at approximately 560 nm) may be generated. In general, the visible light image (i.e. the first image) may be built from whichever camera outputs are not being used for FL imaging. Color balancing can be performed knowing the illumination light wavelength distribution and the filter characteristics of the prism.

For example, a camera head and a microscope assembly, such as the microscope shown in connection with FIGS. 1a to 2b, 4a to 7, may comprise such an optical beam splitter assembly.

The above apparatus may be further improved by adding one or more of the features that are described in the following. Each of the following features may be added to the apparatus independently of the other features. Moreover, each feature has its own advantageous technical effect, as is explained hereinafter.

The first beam splitter can reflect light of the first spectral portion along the first light path. This can guide light of the first spectral portion along the first light path.

Similarly, the second beam splitter can reflect light of the second spectral portion along the second light path. This can guide light of the second spectral portion along the second light path.

The first beam splitter may transmit light of the second spectral portion. This can make the configuration simple.

The second beam splitter may transmit light of the first spectral portion. Again, this can make the configuration simple.

In a further embodiment, the second beam splitter can be such that it does not transmit the first spectral portion. In particular, the light reaching the second beam splitter can be such that it does not comprise the first spectral portion. In such a case, it is not necessary for the second beam splitter to have any particular properties for light of the first spectral portion. It could absorb or reflect such light.

In order to record an image of a characteristic tissue or region, for at least one of the first and the second light paths, an emission band of a fluorophore may overlap with the corresponding spectral portion.

In an advantageous embodiment, at least one beam splitter is a dichroic mirror. This can simplify the set-up. The dichroic mirror can be such that it reflects a certain wavelength at a specified angle. The dichroic mirror can comprise a layer or a coating of a defined uniform thickness. The dichroic mirror can also comprise more than one layer to select more than one wavelength.

At least one of the spectral portions of the light guided by the first light path and the second light path may comprise two spectral subportions spaced apart from each other. This can facilitate a recording of two distinct signals at one light output section. For example, two different fluorescence emission bands can be visualized and distinguished on one camera chip.

The optical beam splitter assembly can be configured for use with at least two fluorophores, each of the two fluorophores having a different fluorescence emission band, wherein for each spectral subportion, a fluorescence emission band of a fluorophore overlaps with the spectral subportion and/or lies within the spectral subportion. This can allow for a recording of images associated with the two fluorophores. The two fluorophores can be fluorescein and ICG.

The optical beam splitter assembly can further comprise at least one camera for detecting the light at one of the first, second and third output sections. The camera can comprise an image sensor. The camera and/or the image sensor can be arranged at the first, second or third output section, respectively.

At least one camera may comprise a Bayer filter. Such camera can also be designated as color camera. This can help to record images, in particular when the corresponding spectral portion is wide and/or different spectral portions have to be differentiated, for example different fluorescence emission bands.

In an advantageous embodiment, a subfilter of the Bayer filter is selected to match a fluorescence emission band of one of the fluorophores. This increases the signal intensity. In particular, a maximum of the transmittance of the subfilter can be located within 50 nm, preferably within 20 nm of a wavelength of the maximum of the fluorescence emission band. For example, one subfilter can have a maximum of transmission at 560 nm to match fluorescein. A further subfilter can have a maximum at 850 nm to match ICG (Indocyanine Green). In some implementations, the Bayer filters have standardized wavelength ranges for each color. In this case, the fluorescence emissions in the wavelength band around 560 nm are only seen by the green channel, while the infra-red fluorescent signal passes through the Bayer filter and is detected on all channels (RGB). This differential response enables the two fluorescence emission wavelengths to be distinguished.

A transmittance of the subfilter at the wavelength of the maximum of the fluorescence emission band can be more than 80 percent, preferably more than 90 percent, especially more than 95 percent.

In order to maximize the yield, a fluorophore can be selected so that its fluorescence emission band overlaps with the spectral portion transmitted by a subfilter of the Bayer filter.

To achieve a high sensitivity, at least one camera can be a black-and-white camera without a Bayer filter, in contrast to the other cameras, where the Bayer filters enable color imaging by enabling the separation of different color channels. The losses occurring due to the subfilters of the Bayer filter can then be avoided. The black-and-white camera can comprise a black-and-white image sensor. The black-and-white image sensor can also be named a grey image sensor as it can measure different intensities which correspond to shades of grey if displayed on a monochrome display.

In an advantageous embodiment, the optical beam splitter assembly comprises three cameras, one camera being a black-and-white camera without a Bayer filter and two cameras comprising Bayer filters. The two cameras with the Bayer filters allow differentiating between different wavelengths while the black-and-white camera can provide a high sensitivity for example for weak signals.

In one embodiment, the black-and-white camera without the Bayer filter can be arranged at the second light output section. Further, the cameras with the Bayer filters can be arranged at the first and the third light output sections.

In another embodiment, the camera with the black-and-white image sensor and without the Bayer filter can be arranged at the first light output section. Further, the cameras with the Bayer filters can be arranged at the second and the third light output sections.

In a preferred development, an image sensor and/or a camera associated with the first light output section is configured to record a color image in a color space, the color space having a predetermined set of color channels, wherein the spectral portion of the first light path comprises two spectral subportions, wherein a first subportion overlaps with a first color channel of the color space and not a second color channel of the color space, wherein a second subportion overlaps at least with the second color channel. This can facilitate a separation of the signals by simply selecting one of the color channels.

The first subportion can be associated with fluorescein and the first color channel can be a green channel. Green can in particular relate to the portion of 500-565 nm.

The second subportion can be associated with ICG and the second color channel can be a red channel. Red can in particular relate to the portion of above 625 nm.

When specifying the wavelength, this can in particular relate to the wavelength in a vacuum. In a medium, the wavelength can be shorter. The frequency in different media can remain the same and the product of wavelength times frequency can be the speed of light in the medium.

The two color channels may be separated by another color channel. This can allow for an easy recording of the distinct images as cross-talk between the color channels is minimized.

In an easy-to-apply configuration, the color channel is a primary color. In particular, the color space may be an RGB color space with red, green and blue as the primary colors.

Preferably, the optical beam splitter assembly is configured for guiding light of two fluorescence emission bands with a first and a second wavelength to the first light output section and light of a fluorescence emission band with a third wavelength between the first and the second wavelength to the second light output section. The damping of the first and the second wavelength is then minimal.

In a further embodiment, the image sensor and/or the camera associated with the second output section can be configured to record a color image in a color space, the color space having a predetermined set of color channels and the spectral portion of the first light path comprises two spectral subportions, wherein a first subportion overlaps with a first color channel of the color space and not a second color channel of the color space, wherein a second subportion overlaps at least with the second color channel. The first subportion can again be associated with fluorescein and the first color channel can be a green channel. The second subportion can be associated with ICG and the second color channel can be a red channel.

The optical beam splitter assembly can be configured for guiding light of two fluorescence emission bands with a first and a second wavelength to the second light output section and light of a fluorescence emission band with a third wavelength between the first and the second wavelength to the first light output section. This can allow a good separation of the fluorescence emission bands.

The spectral portion recorded by the image sensor and/or the camera associated with the second light output section can lie between the two spectral subportions recorded at the first light output section. This can allow a good separation of the portions.

In particular, the optical beam splitter assembly can be configured to guide white light to the third output section. The white light can be the portion of the light that remains when the first and the second portion are filtered out. The white light can be the third portion. This white light can be used to produce an image that gives an overview of an area where surgery is performed.

At least one beam splitter can comprise a coating on a prism. This can give a compact configuration.

In an advantageous embodiment, the optical beam splitter assembly comprises at least one of a first prism comprising the light entrance section and the first light output section, a second prism comprising the second light output section, and a third prism comprising the third light output section. This can have the effect that the optical beam splitter assembly can be compact.

The first beam splitter may be between the first prism and the second prism to achieve a solid configuration. Similarly, the second beam splitter may be between the second prism and the third prism.

In a further development that results in a space-saving and solid arrangement, the optical beam splitter assembly comprises three prisms that are connected to each other to form a unitary block. The block can be monolithic.

In an advantageous embodiment, the first and the second spectral portion do not overlap. Thus, the signal strength is improved.

Similarly, the first, the second and the third spectral portion do not overlap in an advantageous embodiment.

The optical beam splitter assembly can be configured for the combined use of fluorescein, ICG and 5-ALA. This can for example be achieved when a first subportion and a second subportion of a first portion and a second portion are such that each of them overlaps with one fluorescence emission band of fluorescein, ICG and 5-ALA but not with the fluorescence emission bands of the other fluorophores.

A microscope assembly can further comprise an image processing device, wherein the image processing device is configured to create a single image from three images from the three light output sections.

The beam splitter arrangement can be used to distinguish three fluorescent wavelength bands and generate a visible arrangement. In principle, the arrangement can be used for all four images simultaneously with appropriate illumination.

The visible image is built from whichever camera outputs are not being used for fluorescence (FL) imaging. Color balancing can be performed knowing the illumination light wavelength distribution and the filter characteristics of the prism/beam splitter arrangement.

In an advantageous microscope assembly, a user can select or indicate a fluorescence mode. Illumination by an illumination source can be controlled by a controller to provide appropriate excitation illumination (one or more of a first fluorescence illumination light, a second fluorescence illumination light and a third fluorescence illumination light), plus a broad band "white light" illumination. The system can then know the signals of which camera or cameras relates to the selected fluorescence, and which to use in order to construct a color-balanced visible image. One or more images can then be output to alternative displays. Such a color-balancing can be performed in an image processing device.

The suitability for recording an image does not necessarily include saving of the image. The inventive solution can also be used if an image is captured and for example processed and displayed live on one or more displays, but not saved afterwards.

Next, several embodiments are further described by way of examples only using sample embodiments, which are also shown in the drawings. In the drawings, the same reference numerals are used for features which correspond to each other with respect to at least one of function and design.

The combination of features shown in the enclosed embodiments is for explanatory purposes only and can be modified. For example, a feature of the embodiment having a technical effect that is not needed for a specific application may be omitted. Likewise, a feature which is not shown to be part of the embodiment may be added if the technical effect associated with this feature is needed for a particular application.

Figures 1, 4A:
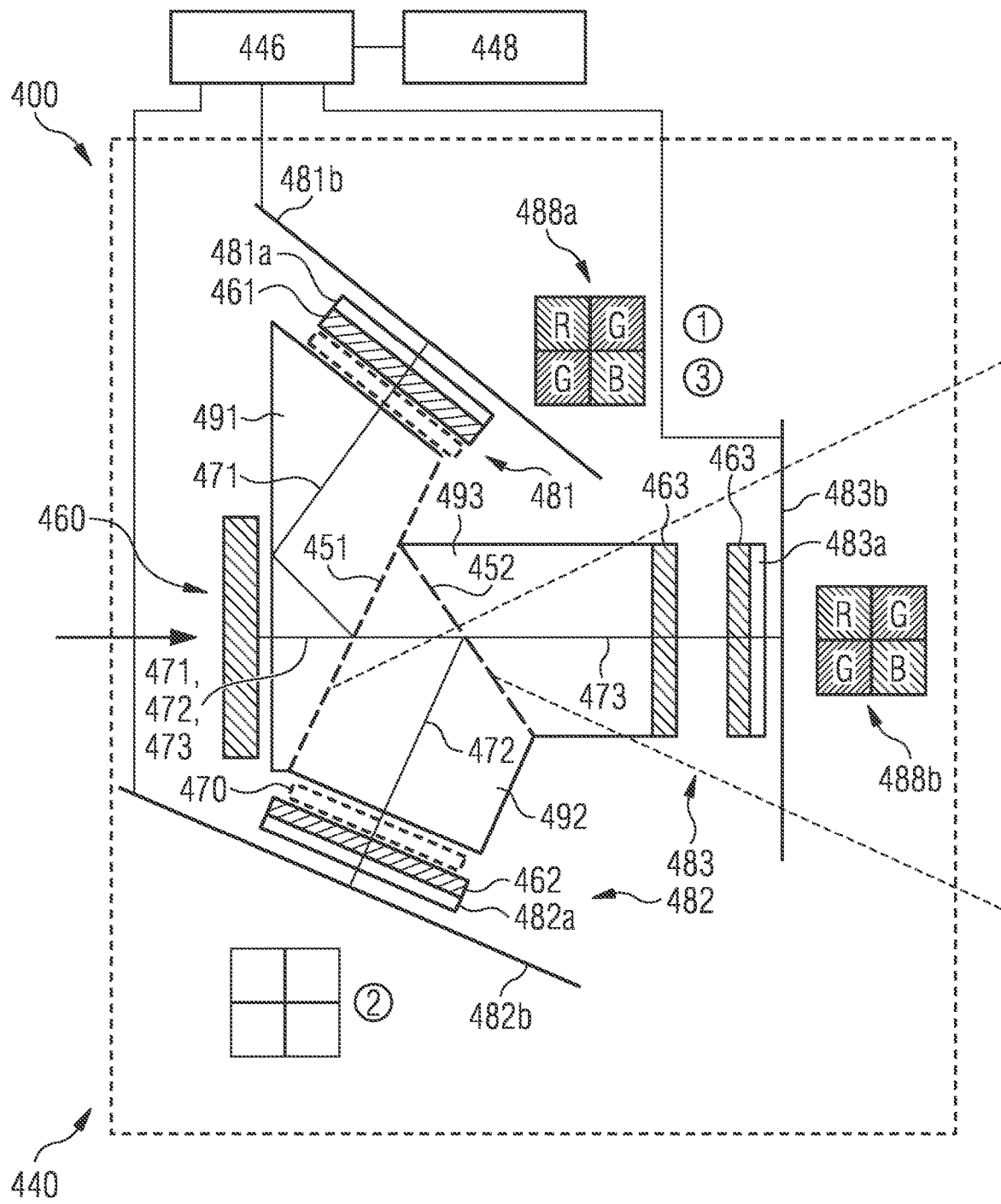
FIG. 4a shows a schematic representation of an embodiment of a microscope assembly comprising an embodiment of an optical beam splitter assembly.
Figures 2, 4A:
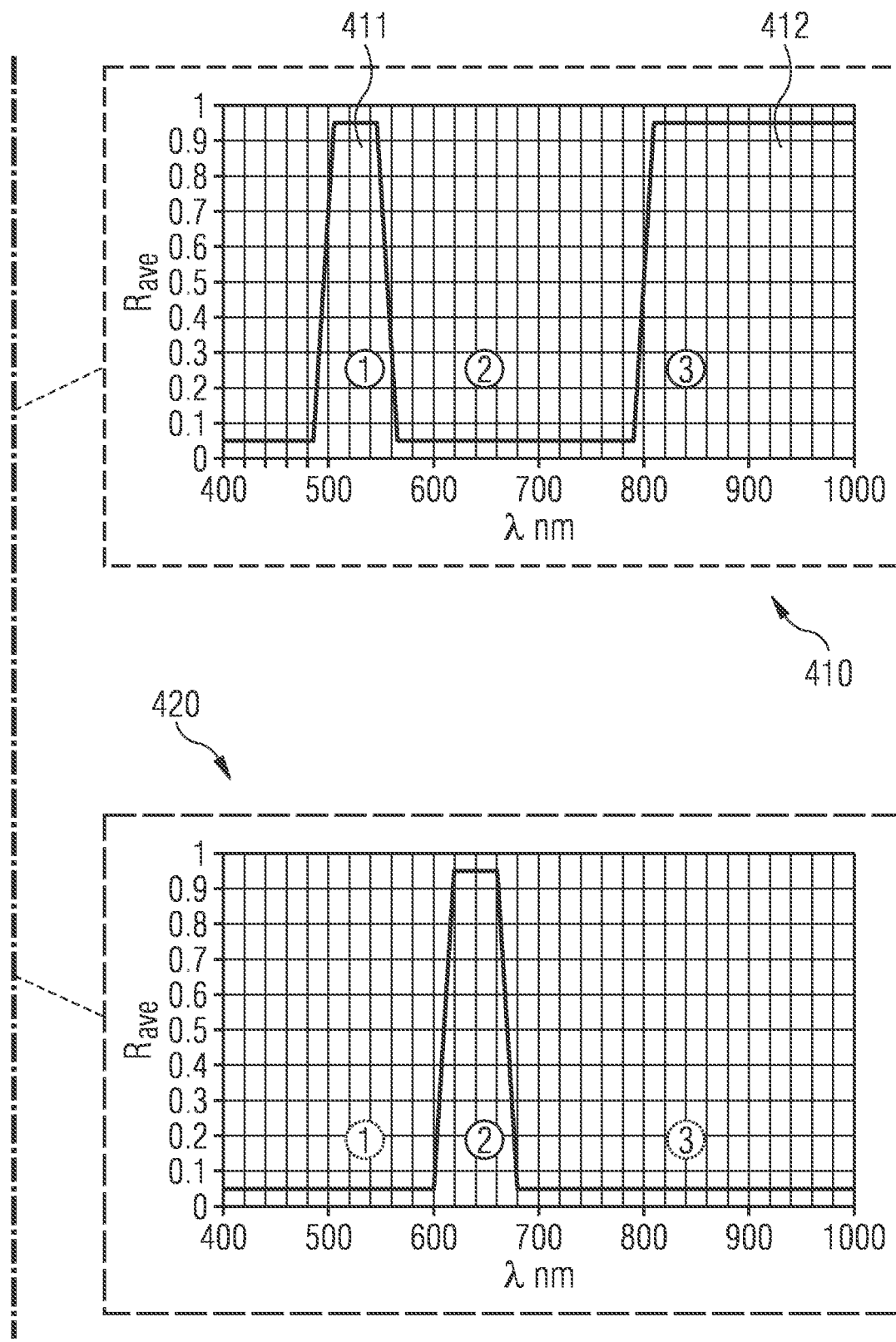

In FIG. 4a, a microscope assembly 445 (which may correspond to the microscope system 1000 of FIG. 1a or to one of the microscopes shown in connection with FIGS. 1a to 2b, 6a to 7) comprising a beam splitter assembly 400 (which may correspond to the beam splitter assembly 132 shown in FIG. 1c) is shown. The beam splitter assembly 400 allows to take and record images of an area in which surgery is performed.

Three cameras 481, 482, 483 (which may correspond to or comprise the image sensors 134-1-34-3 shown in FIG. 1c) are present that are suitable for recording images of different spectral portions 410, 420, 430. In FIG. 4a, lines 481b, 482b and 483b show the actual camera sensors, with 481a, 482a and 483a showing bandpass filters configured to limit the light incident to the camera sensors to the desired portions of the spectrum. By this, fluorescences from different fluorophores can be imaged separately. The images acquired in this way can then be input into an image processing device 446 of the microscope assembly and be combined as desired. For example, two or three images can be overlaid and combined into a single image in which characteristic tissue can be seen by a surgeon. The intensities of the signals of the fluorophores might be adjusted as desired and for example be displayed with false colors to allow an easy differentiation. Such an image can then be displayed on a display device 448 or viewed in a viewing system. In front of the bandpass filters, dummy glass may be used, herein also acting as light output sections 461, 462, 463. The dummy glass blocks may be used to ensure that the optical path length to each camera is identical. The light coming into the prism is converging (focused) so the focus may be directed at each camera surface. Additionally, optional glass dummies 170 can be present at the light output sections.

The optical beam splitter assembly 400 comprises a first beam splitter 451 (132-1 in FIG. 1c) and a second beam splitter 452 (132-2 in FIG. 1c). The two beam splitters 451, 452 serve to split the light into a first light path 471, a second light path 472, and a third light path 473.

The first light path 471 is configured to guide light of a first spectral portion 410 from a light entrance section 460, at which the light (visible light/reflected light and fluorescence emissions) enters the optical beam splitter assembly 400, to a first light output section 461.

Similarly, the second light path 472 is configured to guide light of a second spectral portion 420 from the light entrance section 460 to a second light output section 462, the second light output section 462 being spaced apart from the first light output section 461.

Finally, the third light path 473 is configured to guide light of a third spectral portion 430 from the light entrance section 460 to a third light output section 463, the third light output section 463 being spaced apart from the first light output section 461 and the second light output section 462.

The second light path 472 traverses the first beam splitter 451, and the third light path 473 traverses the first and the second beam splitter 451, 452.

The beam splitters 451, 452 can be each embodied as dichroic mirrors 455. Each dichroic mirrors 455 comprises at least one thin layer that reflects a predefined wavelength under a certain angle. Other wavelengths can be transmitted.

The first beam splitter 451 reflects light of the first spectral portion 410 along the first light path 471. The first beam splitter 451 transmits light of the second spectral portion 420 and further wavelengths that are not part of the first spectral portion 410. Similarly, the second beam splitter 452 reflects light of the second spectral portion 420 along the second light path 472 and can for example transmit other wavelengths. As no or almost no light of the first spectral portion 410 arrives at the second beam splitter 452, it could however also reflect light of the first spectral portion 410.

The optical beam splitter assembly 400 comprises three cameras 481, 482, 482 having three image sensors 481b, 482b, 483b for detecting the light at the first, second and third output section 461, 462, 463. To this end, the three image sensors 481b, 482b, 483b are arranged at the first, second or third output section 461, 462, 463, respectively. The image sensors are coupled with bandpass filters 481a, 482a and 482b. In some implementations, the coating of the beam splitters does not match the ideal distribution shown in the graphs, so the bandpass filters may be used to block (any) light outside the desired bands.

In order to record signals coming from the characteristic tissue and the fluorophores, for at least one of the first and the second light paths 471, 472 an emission band of a fluorophore overlaps with the spectral portion 410, 420. For example, at least one of fluorescein, 5-ALA and ICG can be used as a fluorophore.

In the depicted embodiment, the spectral portion 410 of the light guided by the first light path 471 comprises two spectral subportions 411 (marked with a 1 in a circle), 412 (marked with a 2 in a circle) spaced apart from each other. This can be, for example, achieved by a first beam splitter 451 that reflects two spectral subportions and guides them onto the first image sensor 481a of the first camera 481 located at the first light output section 461.

For each spectral subportion 411, 412, a fluorescence emission band of a fluorophore overlaps with the spectral subportion 411, 412 or lies within the spectral subportion 411, 412. In particular, in this example, the first spectral subportion 411 associated with fluorescein is located around the typical fluorescence emission wavelength of 540 nm. The second spectral subportion 412 associated with ICG comprises wavelengths of around 750-900 nm.

The first camera 481 comprises a Bayer filter 488a. The Bayer filter 488a comprises three subfilters for selectively transmitting only one of red, green and blue onto each pixel. The area of the green subfilter comprises the combined area of the red and the blue subfilter. By using such a Bayer filter 488a, the two subportions 411, 412 relating to the two fluorophores can be separated easily. For example, fluorescence emissions caused by fluorescein can be detected using the pixels coupled with the green subfilters. Fluorescence emissions caused by ICG are visible at each pixel, and can thus be identified using computational logic. The two subportions 411, 412 are spaced apart from each other so that a cross talk between them is minimized. This means that a fluorescence signal, which has a natural bandwidth, has only a very small or no signal strength at the other subportion.

A subfilter of the Bayer filter 488a can be selected to match to a fluorescence emission band of one of the fluorophores. In particular a maximum of the transmittance of the subfilter can be located within 50 nm, preferably 20 nm of the fluorescence emission band maximum. A transmittance of the subfilter at the wavelength of the maximum of the fluorescence emission band can be more than 80 percent, preferably more than 90 percent, even more preferably at least 95 percent.

Advantageously, a fluorophore is selected so that its fluorescence emission band overlaps with the spectral portion transmitted by a subfilter of the Bayer filter 488a.

In order to achieve a high sensitivity, the second camera 482 comprises a black-and-white image sensor 482a, but not a Bayer filter. This can for example be useful when a weak signal or a fluorophore with a low quantum efficiency is used. For example, the second light path 472 can be associated with a spectral portion 420 relating to a fluorescence emission of 5-ALA.

The third camera 483 can comprise a Bayer filter 488b and a third image sensor 483a in order to record the third spectral portion 430 of remaining light which has a broad spectral range and can be denominated white light. This third spectral portion 430 can be used to give a general overview of the area in which surgery is performed (with the field of view of the images being the same). In various modes of operation, the third spectral portion is combined one of the other spectral portions (not being used for fluorescence imaging) to generate a visible light image.

In total, the optical beam splitter assembly 400 comprises three cameras 481, 482, 483, one camera 482 being operated without a Bayer filter (and thus operating in effect as a black-and-white image sensor) and two cameras 481, 483 comprising Bayer filters 488a, 488b. The two cameras 481, 483 comprising Bayer filters 488a, 488b can also comprise black-and-white image sensors 481a, 483a behind the Bayer filters 488a, 488b. The two cameras 481, 483 can be color cameras that allow to take images with color information.

In the depicted embodiment, the image sensor 482a of the camera 482 without a Bayer filter is arranged at the second light output section 462 and the image sensors 481a, 483a of the cameras 481, 483 with the Bayer filters 488a, 488b are arranged at the first and the third light output sections 461, 463. In other embodiments, a camera without a Bayer filter could be arranged at the first output section 461 to avoid any loss due to the first beam splitter 451.

Figure 4B:
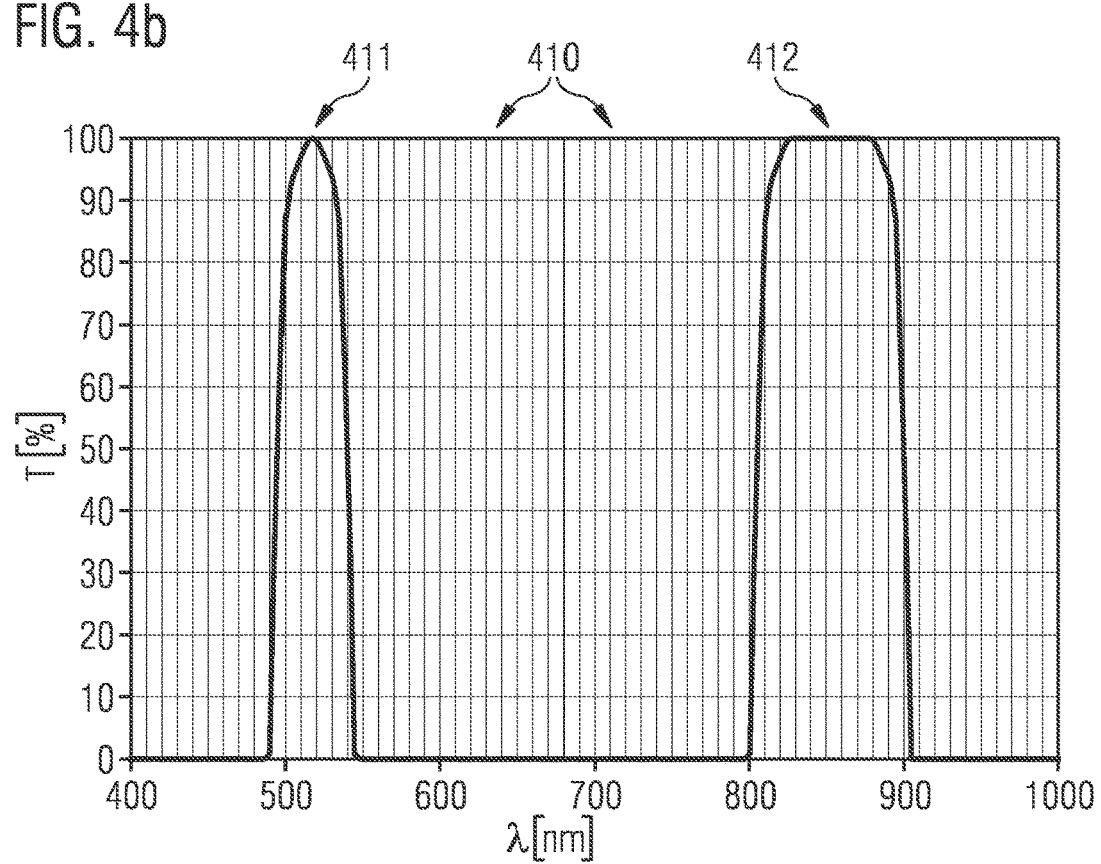
FIG. 4b shows a graph representing the spectral portion arriving at the first light output section when visible and fluorescence light enters the light entrance section.
Figure 4C:
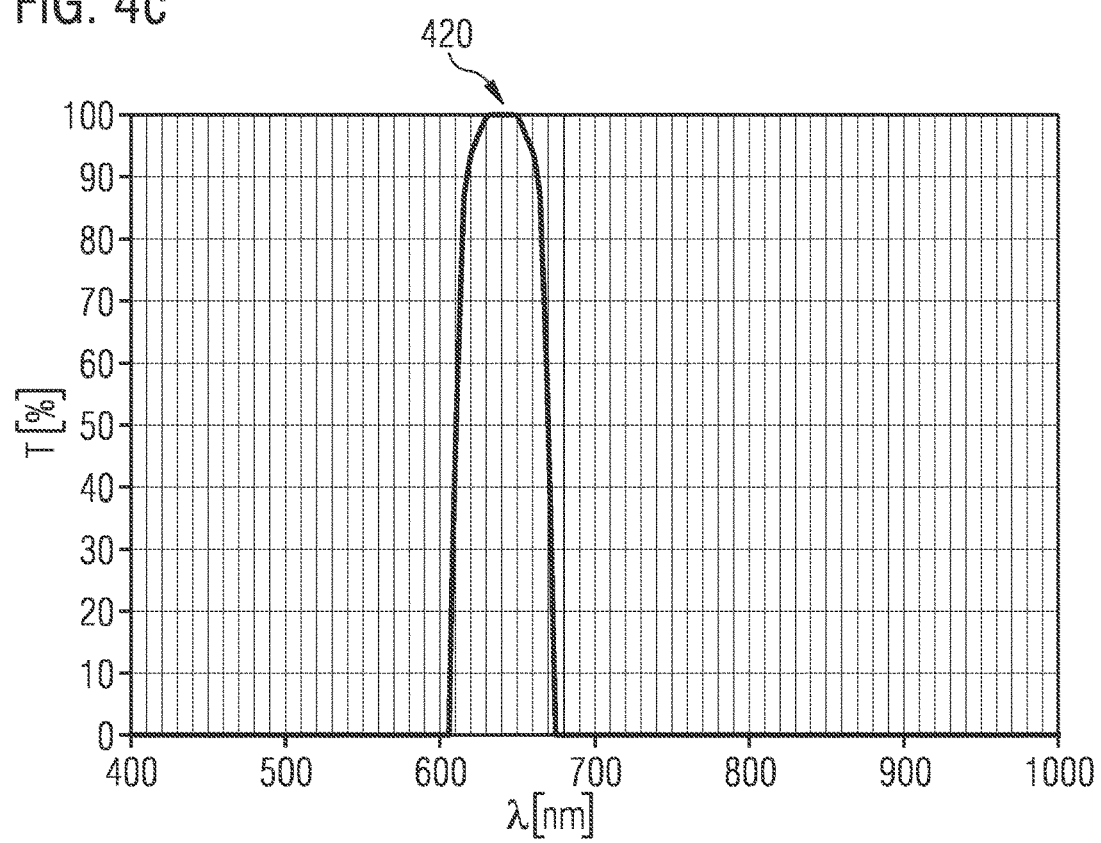
FIG. 4c shows a graph representing the spectral portion arriving at the second light output section when visible and fluorescence light enters the light entrance section.

The camera 481 associated with the first light output section 461 is configured to record a color image in an RGB color space, the color space having a predetermined set of color channels. The spectral portion 410 of the first light path 471 comprises two spectral subportions 411, 412, wherein a first subportion 411, namely the one associated with fluorescein, overlaps with a first color channel, namely green, of the color space but not a second color channel, namely red of the color space. The second subportion 412, namely one related with ICG, overlaps at least with the second color channel, namely red. As shown in FIGS. 4a to 4c, the beam splitter 451 may comprise an average reflectivity ($R_{ave}$) of >90% at 515 nm 535 nm, 835~880 nm, and of <5% at 400 nm~495 nm, 555 nm~810 nm. The beam splitter 452 may comprise an average reflectivity ($R_{ave}$) of >90% at 625 nm~645 nm, and of <5% at 400 nm~605 nm, 665 nm~810 nm. The incident angle may can be F8.0.

The two color channels can be separated by another color channel.

Each of the color channels can be a primary color, for example red, green or blue.

In other words, the reflected spectral portion 420 recorded by the second image sensor 482a associated with the second light output section 462 lies between the two spectral subportions 411, 412 recorded at the first light output section 461. Hence, the first and the second spectral portion 410, 420, do not overlap.

Further, the optical beam splitter assembly is configured to guide white light or remaining light to the third output section 463. The optical beam splitter assembly 400 is configured for guiding light of two fluorescence emission bands with a first and a second wavelength to the first light output section 461 and light of a fluorescence emission band with a third wavelength between the first and the second wavelength to the second light output section 462.

Figure 4D:
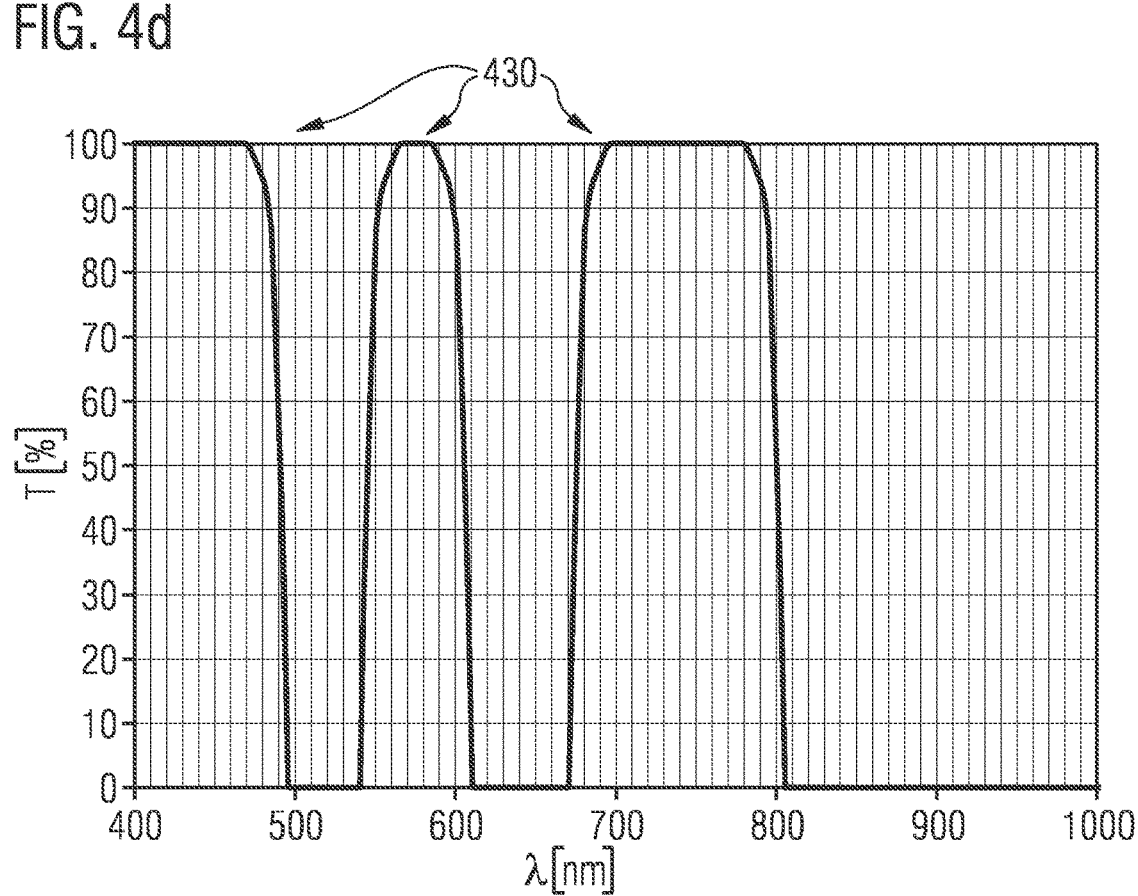
FIG. 4d shows a graph representing the spectral portion arriving at the third light output section when visible and fluorescence light enters the light entrance section.

The resulting distribution of the different spectral portions can be seen in FIGS. 4b to 4d. In this case, light with wavelengths below approximately 900 nm enters the optical beam splitter assembly 400 through the light entrance section 460. The fluorescein band and the ICG band are directed towards the first camera 481 by the first beam splitter 451 and can in FIG. 4b be seen as two distinct peaks in the spectrum with a gap between the two peaks.

The 5-ALA peak is transmitted through the first beam splitter 451 and directed by the second beam splitter 452 towards the second camera 482. Due to the lack of a (Bayer) filter in the second camera 482, a high sensitivity can be achieved for this weak signal. As can be seen in FIG. 4c, this peak is located between the two peaks measured at the first output section. This separation of the peaks allows a good separation and reliable detection of the signals.

In FIG. 4d, the portion of the light that arrives at the third output section 463 is shown. This is the light that enters the input section and is neither deflected towards the first output section 461 nor towards the second output section 462 nor absorbed. Due to the width of the spectrum, this portion can be named white light.

In a different embodiment, an image sensor 482a and/or a camera 482 associated with the second output section 462 could be configured to record a color image in a color space, the color space having a predetermined set of color channels and the spectral portion 420 of the second light path 472 comprises two spectral subportions wherein a first subportion overlaps with a first color channel of the color space and not a second color channel of the color space, wherein a second subportion overlaps at least with the second color channel.

In the present example, the optical beam splitter assembly is configured for guiding light of two fluorescence emission bands with a first and a second wavelength to the second light output section 462 and light of a fluorescence emission band with a third wavelength between the first and the second wavelength to the first light output section 461.

The two beam splitters 451, 452 each comprise a coating 495 on a prism 491, 492, 493.

Further, the optical beam splitter assembly 400 comprises a first prism 491 comprising the light entrance section 460 and the first light output section 461, a second prism 492 comprising the second light output section 462, and a third prism 493 comprising the third light output section 463.

The first beam splitter 451 is between the first prism 491 and the second prism 492. Moreover, the second beam splitter 452 is between the second prism 492 and the third prism 493.

In total, the optical beam splitter assembly 400 comprises three prisms 491, 492, 493 that are connected to each other to form a unitary block 499. This can simplify the handling. In particular, the optical beam splitter assembly 400 can be part of a camera head 440 of the microscope assembly 445 or the microscope.

The optical beam splitter assembly 400 is configured for the combined use of fluorescein, ICG and 5-ALA. This is achieved as the first subportion 411 and the second subportion 412 of the first portion 410 and the second portion 420 are such that each of them overlaps with one fluorescence emission band of fluorescein, ICG and 5-ALA but not with the fluorescence emission bands of the other fluorophores.

Figures 1, 4E:
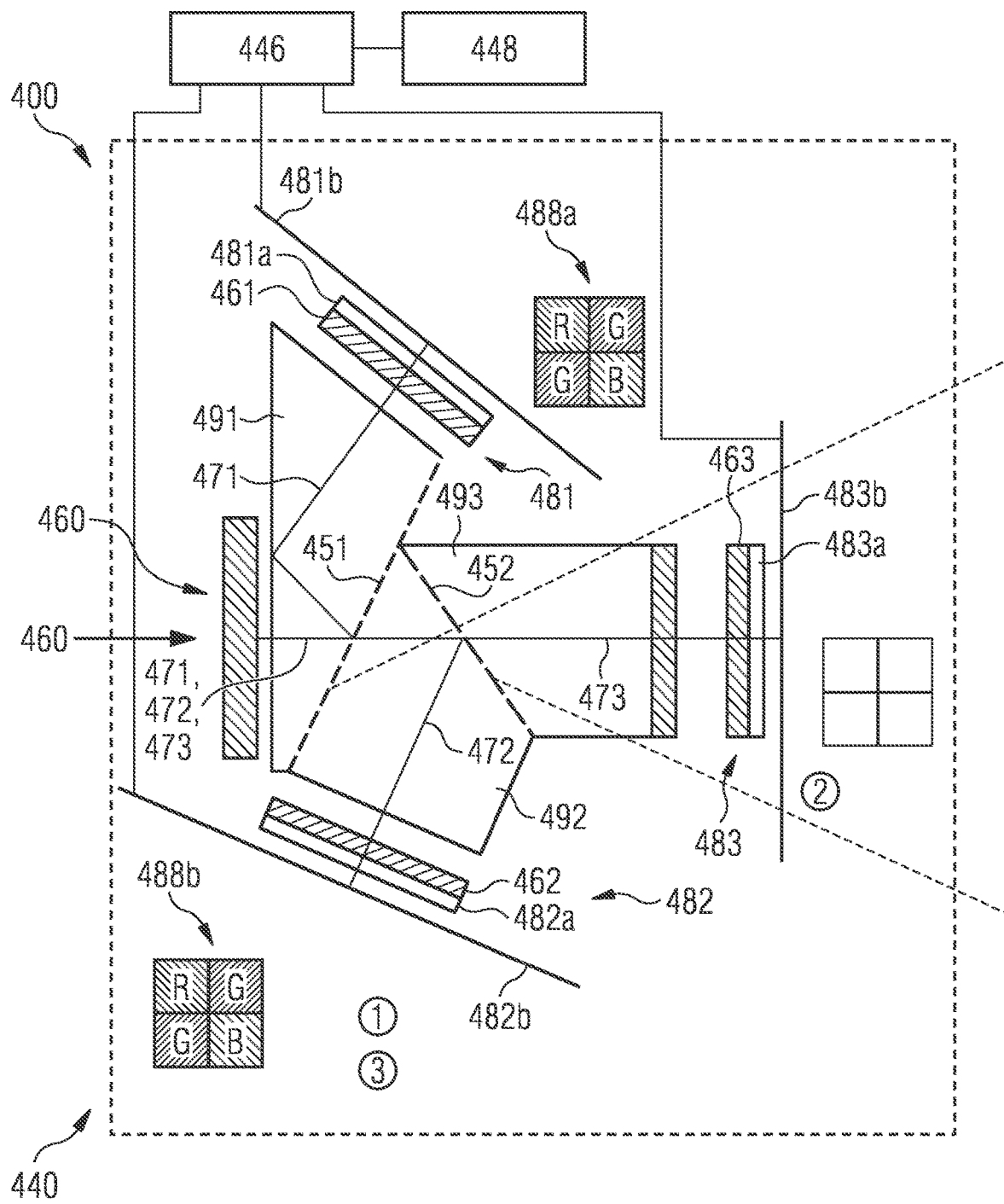
FIG. 4e shows a schematic representation of a further embodiment of a microscope assembly comprising an embodiment of an optical beam splitter assembly.
Figure 4E:
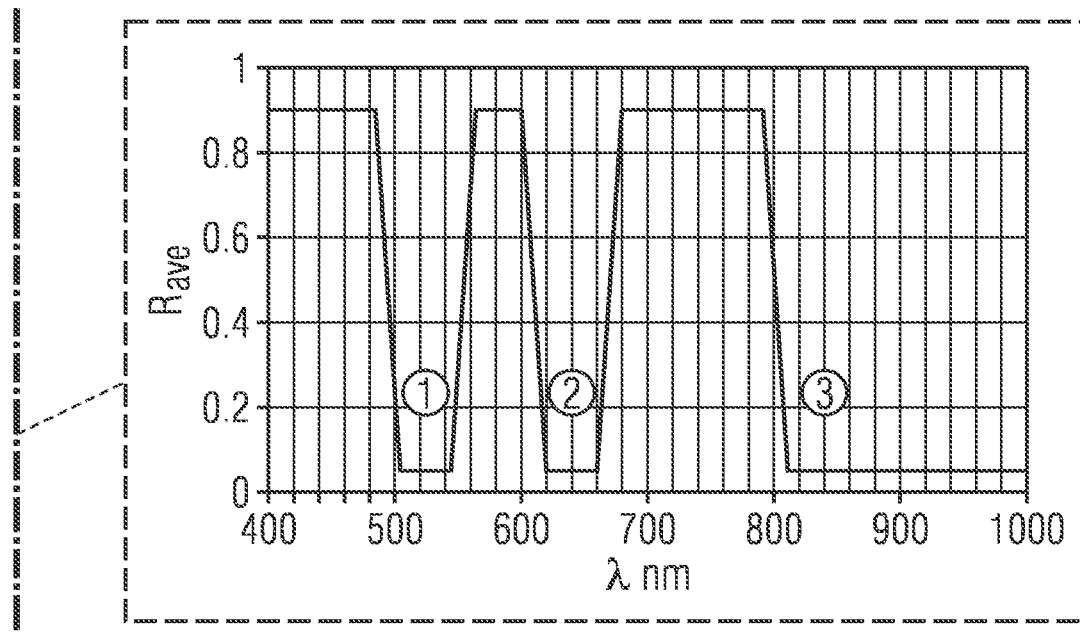
Figure 2:
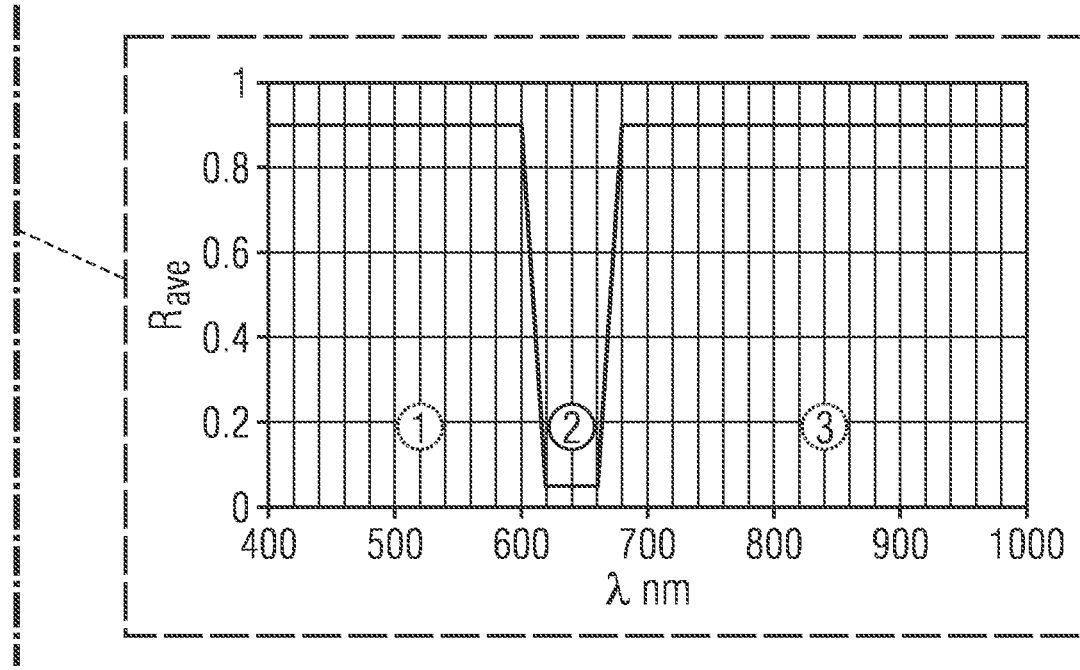

In FIG. 4e, a further embodiment is depicted. Again, three cameras 481, 482, 483 are present that are suitable for recording images of different spectral portions 410, 420, 430. Through this, fluorescences from different fluorophores can be imaged separately. The images acquired in this way can then be input into an image processing device 446 of the microscope assembly and be combined as desired.

The optical beam splitter assembly 400 comprises a first beam splitter 451 and a second beam splitter 452. The two beam splitters 451, 452 serve to split the light into a first light path 471, a second light path 472, and a third light path 473.

For the first beam splitter 451, the average reflectivity can be $R_{ave}$>90%@400 nm~485 nm, 565 nm~599 nm, 679 nm~790 nm, $R_{ave}$<5%@505 nm~545 nm, 619 nm~659 nm, 810 nm~850 nm. This means that the average reflectivity is greater than 90% in the intervals from 400 nm to 485 nm, 565 nm to 599 nm, and 679 nm to 790 nm and less than 5% in the intervals 505 nm to 545 nm, 619 nm to 659 nm, and 810 nm to 850 nm. The incident angle can be F8.0.

For the second beam splitter, the average reflectivity can be $R_{ave}$>90%@400 nm~599 nm, 679 nm~850 nm, $R_{ave}$<5%@619 nm~659 nm. This means that the average reflectivity is greater than 90% in the intervals from 400 nm to 599 nm, and 679 nm to 850 nm and less than 5% in the interval 619 nm to 659 nm. The incident angle can be F8.0.

Thus, the first beam splitter 451 transmits the signals of all three fluorophores Fluorescein, 5-ALA and ICG. Other light is reflected onto the first camera 481, which comprises a first Bayer filter 488a. The second beam splitter 452 transmits only the 5-ALA signal, which then arrives at the third camera 483, which comprises a black-and-white image sensor 483a and no Bayer filter. The signals for Fluorescein and ICG are reflected onto the second camera 482 by the second beam splitter, which comprises a Bayer filter 488b.

Figure 5:
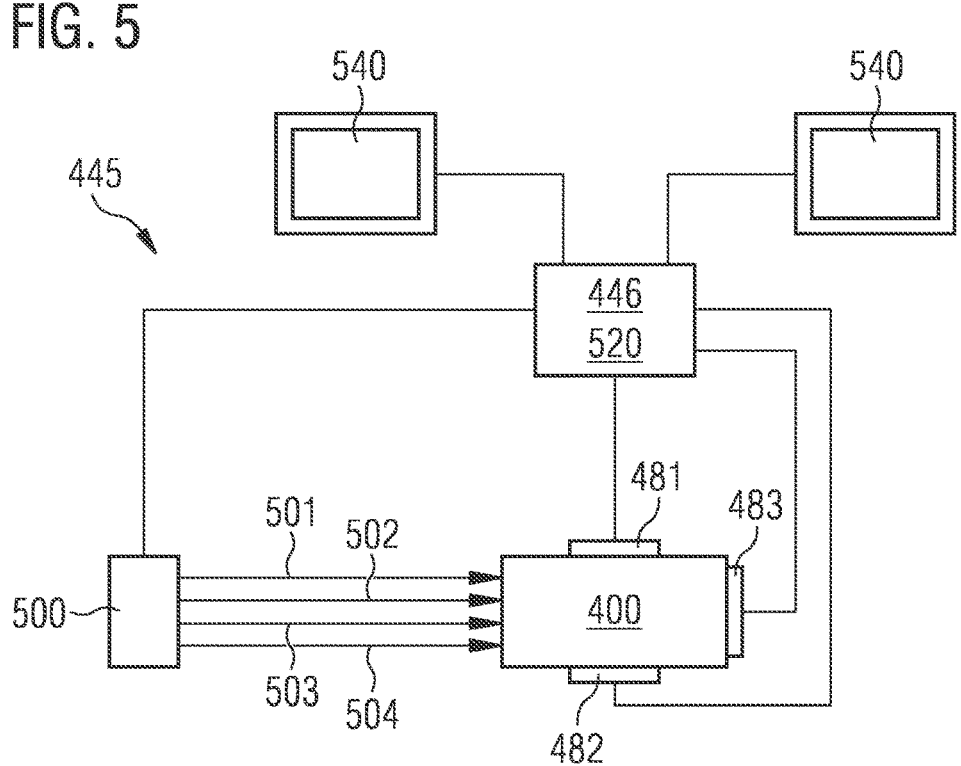
FIG. 5 shows a schematic representation of a further embodiment of a microscope assembly.

In FIG. 5, an advantageous microscope assembly 445 is depicted. A user can select or indicate a fluorescence mode. Illumination by an illumination source 500 will be controlled by a controller 520 to provide appropriate excitation illumination (one or more of a first fluorescence illumination light 501, a second fluorescence illumination light 502 and a third fluorescence illumination light 503), plus a broad band "white light" illumination 504. The system will then know the signals of which camera or cameras 481, 482, 483 relates to the selected fluorescence, and which to use in order to construct a color-balanced visible image. One or more images can then be output to alternative displays 540. Such a color-balancing can be performed in an image processing device 446.

More details and aspects of the microscope assembly or beam splitter assembly are mentioned in connection with the proposed concept or one or more examples described above or below (e.g. FIG. 1a to 3, 6a to 7). The microscope assembly or beam splitter assembly may comprise one or more additional optional features corresponding to one or more aspects of the proposed concept or one or more examples described above or below.

In FIGS. 6a to 6d, different illumination modes and imaging modes are shown for an exemplary implementation of the microscope system.

In FIGS. 6a to 6d an optical layout of a microscope system comprising an illumination system 630, which may correspond to the LED-based illumination system 180, an optical subsystem 635, 636, 637, 638 comprising lenses 635, 637 and 638 and a prism 636, a beam-splitter assembly 400, which may correspond to the beam-splitter assembly 132, and three image sensors 481, 482, 483, two of which are operated with Bayer filters 488a/488b (which may correspond to Bayer filters 136-1, 162, is shown. For example, the beam splitter assembly may be implemented similar to the beam splitter assembly shown in connection with FIG. 4e/FIG. 1c.

In FIG. 6a, the operation of the microscope system in visible mode is shown. In FIG. 6a, a white light LED (e.g. a single chip) of the illumination system 630 emits a spectrum 631 in the visible range and illuminates the field of view, which two 3-chip cameras (each comprising the beam-splitter assembly with the three image sensors) observe through two stereoscopic optical systems. Each of these sensors records a specific spectrum 601; 602; 603. Sensor 1 481 records a spectrum 601 in a range from 495 nm-550 nm and from 800 nm-900 nm, Sensor 2 482 records a spectrum 602 from 480 nm-495 nm, 550 nm-615 nm and 665-750 nm. Sensor 3 483 records a spectrum 603 from 615 nm-665 nm. To increase its sensitivity, sensor 3 operates without a Bayer pattern. In visible light operation, the images of all three sensors are combined to create a visible image 610.

In FIG. 6b, the operation of the microscope system in a mode of operation that provides fluorescence emissions in a second frequency range (shown by the number 2 in a circle) is shown. This mode of operation is denoted "FL 400", due to the fluorescence excitation wavelength being close to 400 nm). In FIG. 6b, a white light LED (e.g. a single chip) of the illumination system 630 emits a spectrum and illuminates the field of view. A spectrum 632b within the range between 615 nm-665 nm is blocked, by a bandpass filter, as this covers a typical emission range of 5-ALA. An additional blue led of the illumination system 630 with a peak 632a at 405 nm emits fluorescence excitation power. The resulting spectrum 632 is shown in FIG. 6b. Two 3-chip cameras observe through two stereoscopic optical systems the field of view. Each of these sensors records a specific spectrum 601; 602; 603. Sensor 1 481 records a spectrum 601 in a range from 495 nm-550 nm and from 800 nm-900 nm, Sensor 2 482 records a spectrum 602 from 480 nm-495 nm, 550 nm-615 nm and 665-750 nm. Sensor 3 483 records a spectrum 603 from 615 nm-665 nm. To increase its sensitivity, sensor 3 operates without a Bayer pattern. The images of sensor 1 and 2 are combined to create a visible image 610. The image of sensor 3 creates a fluorescence image overlay 620 (denoted "FL 400" due to the excitation wavelength being close to 400 nm).

In FIG. 6c, the operation of the microscope system in a mode of operation that provides fluorescence emissions in a first frequency range (shown by the number 1 in a circle) is shown. This mode of operation is denoted "FL 560", due to the fluorescence emission wavelength being close to 560 nm). In FIG. 6c, a white light LED (e.g. a single chip) of the illumination system 630 emits a spectrum and illuminates the field of view. A spectrum 633b within the range between 495 nm-550 nm is blocked, as this covers a typical emission range of Fluorescein. An additional cyan led with a peak 633a at 480 nm and a bandpass filter emits fluorescence excitation power. The resulting spectrum 633 is shown in FIG. 6c. Two 3-chip cameras observe through two stereoscopic optical system the field of view. Each of these sensors records a specific spectrum. Each of these sensors records a specific spectrum 601; 602; 603. Sensor 1 481 records a spectrum 601 in a range from 495 nm-550 nm and from 800 nm-900 nm, Sensor 2 482 records a spectrum 602 from 480 nm-495 nm, 550 nm-615 nm and 665-750 nm. Sensor 3 483 records a spectrum 603 from 615 nm-665 nm. To increase its sensitivity, sensor 3 operates without a Bayer pattern. The images of sensor 2 and 3 are combined to create a visible image. The image of sensor 1 creates the "FL 560" fluorescence image overlay.

In FIG. 6*d*, the operation of the microscope system in a mode of operation that provides fluorescence emissions in a third frequency range (shown by the number 3 in a circle) is shown. This mode of operation is denoted "FL 800", due to the fluorescence emission and excitation wavelength being close to 800 nm). In FIG. 6*d*, a white light LED (e.g. a single chip) of the illumination system 630 emits a spectrum and illuminates the field of view. An additional Near Infra-Red (NIR) LED of the illumination system with a peak 634*a* at 788 nm and a bandpass filter emits fluorescence excitation power. The resulting spectrum 634 is shown in FIG. 6*d*.

Two 3-chip cameras observe through two stereoscopic optical system the field of view. Each of these sensors records a specific spectrum. Each of these sensors records a specific spectrum 601; 602; 603. Sensor 1 481 records a spectrum 601 in a range from 495 nm-550 nm and from 800 nm-900 nm, Sensor 2 482 records a spectrum 602 from 480 nm-495 nm, 550 nm-615 nm and 665-750 nm. Sensor 3 483 records a spectrum 603 from 615 nm-665 nm. To increase its sensitivity, sensor 3 operates without a Bayer pattern. The images of sensor 2 and 3 are combined to create a visible image. The image of sensor 1 creates the "FL 800" fluorescence image overlay.

More details and aspects of the illumination modes or imaging modes are mentioned in connection with the proposed concept or one or more examples described above or below (e.g. FIG. 1*a* to 5, 7). The illumination modes or imaging modes may comprise one or more additional optional features corresponding to one or more aspects of the proposed concept or one or more examples described above or below.

As used herein the term "and/or" includes any and all combinations of one or more of the associated listed items and may be abbreviated as "/".

Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus.

Figure 7:
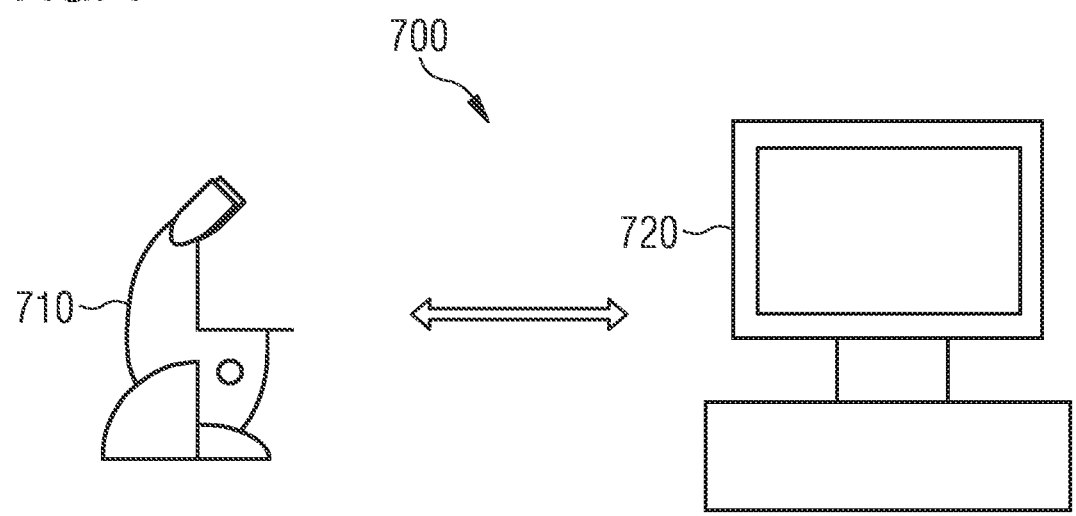
FIG. 7 shows a schematic diagram of an example of a system comprising a microscope and a computer system.

Some embodiments relate to a microscope comprising a system as described in connection with one or more of the FIGS. 1 to 6*d*. Alternatively, a microscope may be part of or connected to a system as described in connection with one or more of the FIGS. 1 to 6*d*. FIG. 7 shows a schematic illustration of a system 700 configured to perform a method described herein. The system 700 comprises a microscope 710 and a computer system 720. The microscope 710 is configured to take images and is connected to the computer system 720. The computer system 720 is configured to execute at least a part of a method described herein. The computer system 720 may be configured to execute a machine learning algorithm. The computer system 720 and microscope 710 may be separate entities but can also be integrated together in one common housing. The computer system 720 may be part of a central processing system of the microscope 710 and/or the computer system 720 may be part of a subcomponent of the microscope 710, such as a sensor, an actor, a camera or an illumination unit, etc. of the microscope 710.

The computer system 720 may be a local computer device (e.g. personal computer, laptop, tablet computer or mobile phone) with one or more processors and one or more storage devices or may be a distributed computer system (e.g. a cloud computing system with one or more processors and one or more storage devices distributed at various locations, for example, at a local client and/or one or more remote server farms and/or data centers). The computer system 720 may comprise any circuit or combination of circuits. In one embodiment, the computer system 720 may include one or more processors which can be of any type. As used herein, processor may mean any type of computational circuit, such as but not limited to a microprocessor, a microcontroller, a complex instruction set computing (CISC) microprocessor, a reduced instruction set computing (RISC) microprocessor, a very long instruction word (VLIW) microprocessor, a graphics processor, a digital signal processor (DSP), multiple core processor, a field programmable gate array (FPGA), for example, of a microscope or a microscope component (e.g. camera) or any other type of processor or processing circuit. Other types of circuits that may be included in the computer system 720 may be a custom circuit, an application-specific integrated circuit (ASIC), or the like, such as, for example, one or more circuits (such as a communication circuit) for use in wireless devices like mobile telephones, tablet computers, laptop computers, two-way radios, and similar electronic systems. The computer system 720 may include one or more storage devices, which may include one or more memory elements suitable to the particular application, such as a main memory in the form of random access memory (RAM), one or more hard drives, and/or one or more drives that handle removable media such as compact disks (CD), flash memory cards, digital video disk (DVD), and the like. The computer system 720 may also include a display device, one or more speakers, and a keyboard and/or controller, which can include a mouse, trackball, touch screen, voice-recognition device, or any other device that permits a system user to input information into and receive information from the computer system 720.

Some or all of the method steps may be executed by (or using) a hardware apparatus, like for example, a processor, a microprocessor, a programmable computer or an electronic circuit. In some embodiments, some one or more of the most important method steps may be executed by such an apparatus.

Depending on certain implementation requirements, embodiments of the invention can be implemented in hardware or in software. The implementation can be performed using a non-transitory storage medium such as a digital storage medium, for example a floppy disc, a DVD, a Blu-Ray, a CD, a ROM, a PROM, and EPROM, an EEPROM or a FLASH memory, having electronically readable control signals stored thereon, which cooperate (or are capable of cooperating) with a programmable computer system such that the respective method is performed. Therefore, the digital storage medium may be computer readable.

Some embodiments according to the invention comprise a data carrier having electronically readable control signals, which are capable of cooperating with a programmable computer system, such that one of the methods described herein is performed.

Generally, embodiments of the present invention can be implemented as a computer program product with a program code, the program code being operative for performing one of the methods when the computer program product runs on a computer. The program code may, for example, be stored on a machine readable carrier.

Other embodiments comprise the computer program for performing one of the methods described herein, stored on a machine readable carrier.

In other words, an embodiment of the present invention is, therefore, a computer program having a program code for performing one of the methods described herein, when the computer program runs on a computer.

A further embodiment of the present invention is, therefore, a storage medium (or a data carrier, or a computer-readable medium) comprising, stored thereon, the computer program for performing one of the methods described herein when it is performed by a processor. The data carrier, the digital storage medium or the recorded medium are typically tangible and/or non-transitionary. A further embodiment of the present invention is an apparatus as described herein comprising a processor and the storage medium.

A further embodiment of the invention is, therefore, a data stream or a sequence of signals representing the computer program for performing one of the methods described herein. The data stream or the sequence of signals may, for example, be configured to be transferred via a data communication connection, for example, via the internet.

A further embodiment comprises a processing means, for example, a computer or a programmable logic device, configured to, or adapted to, perform one of the methods described herein.

A further embodiment comprises a computer having installed thereon the computer program for performing one of the methods described herein.

A further embodiment according to the invention comprises an apparatus or a system configured to transfer (for example, electronically or optically) a computer program for performing one of the methods described herein to a receiver. The receiver may, for example, be a computer, a mobile device, a memory device or the like. The apparatus or system may, for example, comprise a file server for transferring the computer program to the receiver.

In some embodiments, a programmable logic device (for example, a field programmable gate array) may be used to perform some or all of the functionalities of the methods described herein. In some embodiments, a field programmable gate array may cooperate with a microprocessor in order to perform one of the methods described herein. Generally, the methods are preferably performed by any hardware apparatus.

LIST OF REFERENCE SIGNS

100 Microscope
130 Image sensor assembly
132 Beam-splitter assembly
134-1, 134-2, 134-3 Image sensors
136-1, 136-2 Bayer filters
138-1, 138-2, 138-2 Spectral portions
180 Illumination system
181-1 First LED-based light source(s)
181-2 Optical filter
182 Second LED-based light source(s)
183 Third LED-based light source(s)
184 Second optical filter
185 Optical concentration element
190 System for a microscope
192 Interface
194 One or more processors
196 One or more storage devices
310 Emitting radiation power having at least one peak at a wavelength that is tuned to an excitation wavelength of at least one fluorescent material
320 Emitting radiation power across a white light spectrum
330 Generating image data
340 Processing the image data
400 beam splitter assembly
410 first spectral portion
411 first spectral subportion
412 second spectral subportion
420 second spectral portion
430 third spectral portion
440 camera head
445 microscope assembly
446 image processing device
448 display device
451 first beam splitter
452 second beam splitter
455 dichroic mirror
460 light entrance section
461 first light output section
462 second light output section
463 third light output section
471 first light path
472 second light path
473 third light path
481 first camera
481a bandpass filter of first camera
481b first image sensor
482 second camera
482a bandpass filter of second camera
482b second image sensor
483 third camera
483a bandpass filter of third camera
483b third image sensor
488a Bayer filter
488b Bayer filter
491 first prism
492 second prism
493 third prism
495 coating
499 block
500 light source
501 first fluorescence excitation light
502 second fluorescence excitation light
503 third fluorescence excitation light
504 broadband light
520 controller
540 display
601 Spectrum of first sensor
602 Spectrum of second sensor
603 Spectrum of third sensor
610 Visible image
620 Fluorescence image overlay
630 Illumination system
631 Spectrum of the illumination system
632 Spectrum of the illumination system
632a Peak within the spectrum of the illumination system
632b Gap within the spectrum of the illumination system
633 Spectrum of the illumination system
633a Peak within the spectrum of the illumination system
633b Gap within the spectrum of the illumination system
634 Spectrum of the illumination system
634a Peak within the spectrum of the illumination system
700: system (2×)
710: microscope (6×)

720: computer system (12×), receive information from the computer system (1×)

The invention claimed is:

1. A microscope system comprising:
a Light Emitting Diode (LED)-based illumination system, configured to emit radiation power having at least one peak at a wavelength that is tuned to an excitation wavelength of at least one fluorescent material and/or to emit radiation power across a white light spectrum, with the light emitted across the white light spectrum being filtered such that light having a wavelength spectrum that coincides with at least one fluorescence emission wavelength spectrum of the at least one fluorescent material is attenuated or blocked;
at least one image sensor assembly configured to generate image data, the image data representing light reflected by a sample that is illuminated by the LED-based illumination system,
wherein the at least one image sensor assembly comprises a beam-splitter assembly and three image sensors, the beam-splitter assembly being configured to guide light of a first spectral portion to the first image sensor, light of a second spectral portion to the second image sensor and light of a third spectral portion to the third image sensor, the three image sensors being configured to generate image data based on the spectral portions incident to the respective image sensors,
wherein the image data comprises a first portion originating from the first image sensor, a second portion originating from the second image sensor, and a third portion originating from the third image sensor; and
one or more processors, configured to:
process the image data to generate processed image data,
generate a first image representing visible light based on a first combination of the three portions of the image data, and to generate a second image representing fluorescence emissions of the at least one fluorescent material based on a second combination of the three portions of the image data,
wherein the one or more processors are configured to combine the three portions of the image data such that, if light is emitted having one peak at a wavelength that is tuned to an excitation wavelength of one fluorescent material, the first image is generated based on two portions of the image data and the second image is generated based on one portion of the image data, and such that, if light is emitted having three peaks at three wavelengths that are tuned to excitation wavelengths of three fluorescent materials, the first image is generated based on one portion of the image data and the second image is generated based on two portions of the image data.

2. The microscope system according to claim 1, wherein the one or more processors are configured to reconstruct a portion of the processed image data representing light having a wavelength that coincides with the at least one fluorescence emission wavelength of the at least one fluorescent material.

3. The microscope system according to claim 1, wherein the image data represents the light reflected by the sample that is illuminated by the LED-based illumination system and light emitted by the at least one fluorescent material.

4. The microscope system according to claim 1, wherein the one or more processors are configured to generate a first image representing visible light and a second image representing fluorescence emissions of the at least one fluorescent material based on the image data.

5. The microscope system according to claim 1, wherein the LED-based illumination system has two or more modes of operation, the first mode of operation being suitable for reflectance imaging and fluorescence imaging and the second mode of generation being suitable for reflectance imaging, wherein the one or more processors are configured to generate the first image and the second image if the LED-based illumination system operates in the first mode of operation, and to generate the first image without generating the second image if the LED-based illumination system operates in the second mode of operation.

6. The microscope system according to claim 1, wherein a first and a second of the three image sensors are operated with Bayer filters, and a third of the three image sensors is operated without a Bayer filter.

7. A microscope system comprising:
a Light Emitting Diode (LED)-based illumination system, configured to emit radiation power having at least one peak at a wavelength that is tuned to an excitation wavelength of at least one fluorescent material and/or to emit radiation power across a white light spectrum, with the light emitted across the white light spectrum being filtered such that light having a wavelength spectrum that coincides with at least one fluorescence emission wavelength spectrum of the at least one fluorescent material is attenuated or blocked;
at least one image sensor assembly configured to generate image data, the image data representing light reflected by a sample that is illuminated by the LED-based illumination system,
wherein the at least one image sensor assembly comprises a beam-splitter assembly and three image sensors, the beam-splitter assembly being configured to guide light of a first spectral portion to the first image sensor, light of a second spectral portion to the second image sensor and light of a third spectral portion to the third image sensor, the three image sensors being configured to generate image data based on the spectral portions incident to the respective image sensors,
wherein the image data comprises a first portion originating from the first image sensor, a second portion originating from the second image sensor, and a third portion originating from the third image sensor; and
one or more processors, configured to:
process the image data to generate processed image data,
generate a first image representing visible light based on a first combination of the three portions of the image data, and to generate a second image representing fluorescence emissions of the at least one fluorescent material based on a second combination of the three portions of the image data,
wherein the one or more processors are configured to combine the three portions of the image data such, that, if light is emitted having a peak at a first wavelength that is tuned to an excitation wavelength of a first fluorescent material, the second image is generated based on the first portion of the image data, and such that, if light is emitted having a peak at a second wavelength that is tuned to an excitation wavelength of a second fluorescent material, the second image is generated based on the third portion of the image data.

8. The microscope system according to claim 1, wherein the one or more processors are configured to combine the three portions of the image data such, that, if light is emitted having a peak at a third wavelength that is tuned to an excitation wavelength of a third fluorescent material, the second image is generated based on the first portion of the image data.

9. The microscope system according to claim 1, wherein the one or more processors are configured to generate the first image at least based on the second portion of the image data.

10. The microscope system according to claim 1, wherein at least one of the first and the second spectral portion comprises two spectral subportions spaced apart from each other.

11. The microscope system according to claim 1, wherein the first spectral portion comprises two continuous subportions located between 450 nm and 550 nm and between 750 nm and 1000 nm.

12. The microscope system according to claim 1, wherein the third spectral portion is a continuous portion that is located between 550 nm and 700 nm.

13. The microscope system according to claim 1, wherein the LED-based illumination system comprises one or more first LED-based light sources configured to emit radiation power across the white light color spectrum, at least one optical filter that is arranged to filter the light emitted by the one or more first LED-based light sources and configured to attenuate or block light having a wavelength that coincides with the at least one fluorescence emission wavelength of the at least one fluorescent material, and one or more second LED-based light sources configured to emit the radiation power having at least one peak at a wavelength that is tuned to an excitation wavelength of at least one fluorescent material.

14. The microscope system according to claim 13, wherein the one or more second LED-based light sources are configured to emit radiation power having a peak at one or more of
between 390 nm and 420 nm,
between 460 nm and 500 nm, and
between 780 nm and 810 nm.

15. The microscope system according to claim 13, wherein the LED-based illumination system further comprises one or more third LED-based light sources configured to emit radiation power across the white light color spectrum.

16. The microscope system according to claim 1, wherein the LED-based illumination system has two or more modes of operation, wherein the LED-based illumination system is configured to, in a first mode of operation, emit the radiation power having at least one peak at a wavelength that is tuned to the excitation wavelength of at least one fluorescent material and the radiation power across the white light spectrum, with the light emitted across the white light spectrum being filtered such that light having a wavelength that coincides with the at least one fluorescence emission wavelength of the at least one fluorescent material is attenuated or blocked, and, in a second mode of operation, to emit radiation power across the white light spectrum without light having a wavelength that coincides with the at least one fluorescence emission wavelength of the at least one fluorescent material being attenuated or blocked.

17. A method for imaging an object using a microscope, the method comprising:
emitting, using a Light Emitting Diode (LED)-based illumination system, radiation power having at least one peak at a wavelength that is tuned to an excitation wavelength of at least one fluorescent material;
emitting, using the LED-based illumination system, radiation power across a white light spectrum, with the light emitted across the white light spectrum being filtered such that light having a wavelength spectrum that coincides with at least one fluorescence emission wavelength spectrum of the at least one fluorescent material is attenuated or blocked;
generating, using at least one image sensor assembly, image data, the image data representing light reflected by a sample that is illuminated by the LED-based illumination system,
the at least one image sensor assembly comprises a beam-splitter assembly and three image sensors, the beam-splitter assembly being configured to guide light of a first spectral portion to the first image sensor, light of a second spectral portion to the second image sensor and light of a third spectral portion to the third image sensor, the three image sensors being configured to generate image data based on the spectral portions incident to the respective image sensors,
wherein the image data comprises a first portion originating from the first image sensor, a second portion originating from the second image sensor, and a third portion originating from the third image sensor; and
processing the image data to generate processed image data, thereby
generating a first image representing visible light based on a first combination of the three portions of the image data, and to generate a second image representing fluorescence emissions of the at least one fluorescent material based on a second combination of the three portions of the image data,
wherein the one or more processors are configured to combine the three portions of the image data such that, if light is emitted having one peak at a wavelength that is tuned to an excitation wavelength of one fluorescent material, the first image is generated based on two portions of the image data and the second image is generated based on one portion of the image data, and such that, if light is emitted having three peaks at three wavelengths that are tuned to excitation wavelengths of three fluorescent materials, the first image is generated based on one portion of the image data and the second image is generated based on two portions of the image data, and/or
wherein the one or more processors are configured to combine the three portions of the image data such, that, if light is emitted having a peak at a first wavelength that is tuned to an excitation wavelength of a first fluorescent material, the second image is generated based on the first portion of the image data, and such that, if light is emitted having a peak at a second wavelength that is tuned to an excitation wavelength of a second fluorescent material, the second image is generated based on the third portion of the image data.

18. The microscope system according to claim 7, wherein the one or more processors are configured to combine the three portions of the image data such, that, if light is emitted having a peak at a third wavelength that is tuned to an excitation wavelength of a third fluorescent material, the second image is generated based on the first portion of the image data.

* * * * *